(12) United States Patent
Kensch et al.

(10) Patent No.: US 8,673,609 B2
(45) Date of Patent: Mar. 18, 2014

(54) BUTTIAUXELLA SP. PHYTASE VARIANTS

(75) Inventors: Oliver Kensch, Pulheim (DE); Klaus Schulze Pellengahr, Berlin (DE); Birgitta Leuthner, Darmstadt (DE); Jayarama K. Shetty, Pleasanton, CA (US); Michael Pepsin, Castro Valley, CA (US); Søren Dalsgaard, Silkeburg (DK); Mai Faurschou Isaksen, Højbjerg (DK)

(73) Assignee: Danisco US Inc., Palo Alto, CA (US)

( * ) Notice: Subject to any disclaimer, the term of this patent is extended or adjusted under 35 U.S.C. 154(b) by 406 days.

(21) Appl. No.: 12/988,363

(22) PCT Filed: Apr. 17, 2009

(86) PCT No.: PCT/US2009/041011
§ 371 (c)(1),
(2), (4) Date: Jan. 31, 2011

(87) PCT Pub. No.: WO2009/129489
PCT Pub. Date: Oct. 22, 2009

(65) Prior Publication Data
US 2011/0201081 A1    Aug. 18, 2011

Related U.S. Application Data

(60) Provisional application No. 61/046,324, filed on Apr. 18, 2008.

(51) Int. Cl.
*C12N 9/16* (2006.01)
*C07K 14/00* (2006.01)
*C12Q 1/44* (2006.01)
*C12P 21/00* (2006.01)

(52) U.S. Cl.
USPC ............. 435/196; 435/69.1; 435/19; 530/350

(58) Field of Classification Search
USPC ........................... 435/196, 69.1, 19; 530/350
See application file for complete search history.

(56) References Cited

FOREIGN PATENT DOCUMENTS

| EP | 0 813 607 B1 | 2/2004 |
|---|---|---|
| WO | WO 2006/043178 A2 | 4/2006 |
| WO | WO 2008/097619 A2 | 8/2008 |
| WO | WO 2008/097620 A1 | 8/2008 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Berka, R.M., et al., "Molecular Characterization and Expression of a Phytase Gene from the Thermophilic Fungus Thermomyces lanuginosus." Appl. Environ. Microbiol. 64(11): 4423-4427, 1998.
Greiner, R., et al., "Purification and Characterization of Two Phytases from *Escheria coli*." Arch. Biochem. Biophys. 303(1): 107-113, 1993.
Greiner, R., et al., "Purification and Characterization of a Phytase from *Klebsiella terrigena*." Arch. Biochem. Biophys. 341(2): 201-206, 1997.
Kerovuo, J., et al.," Isolation, Characterization, Molecular Gene Cloning, and Sequencing of a Novel Phytase from *Bacillus subtilis*." Appl. Environ. Microbiol. 64(6): 2079-2085, 1998.
Kim, H.W., et al., "Isolation and characterization of a phytase with improved properties from *Citrobacter braakii*." Biotechnol. Lett. 25: 1231-1234, 2003.
Lassen, S., et al., "Expression, Gene Cloning, and Characterization of Five Novel Phytases from Four Basidiomycete Fungi: *Peniophora lycii, Agrocybe pediades*, a *Ceriporia sp.*, and *Trametes pubescens*." Appl. Environ. Microbiol. 67(10): 4701-4707, 2001.
Wyss, M., et al., "Biochemical Characterization of Fungal Phytases (*myo*-Inositol Hexakisphosphate Phosphohydrolases): Catalytic Properties." Appl. Environ. Microbiol. 65 (2): 367-373, 1999.
Yoon, S.J., et al., "Isolation and identification of phytase-producing bacterium, *Enterobacter* sp. 4, and enzymatic properties of phytase enzyme." Enzyme and Microbial Technol. 18: 449-454, 1996.
Zinin, N.V., et al., "Gene cloning, expression and characterization of novel phytase from *Obesumbacterium proteus*." FEMS Microbiol. Lett. 236: 283-290, 2004.
International Search Report and the Written Opinion of the International Searching Authority for International Application No. PCT/US2009/041011 dated Mar. 9, 2010.

* cited by examiner

*Primary Examiner* — Delia Ramirez
(74) *Attorney, Agent, or Firm* — Danisco US Inc.

(57) ABSTRACT

Provided herein are variants of *Buttiauxella* sp. phytases that may be used in industrial applications including methods for starch liquefaction, alcohol fermentations and for enhancing phosphate digestion in foods and animal feeds.

9 Claims, 14 Drawing Sheets

Amino Acid Sequence of Wild-type *Buttiauxella* sp. P1-29 Phytase (SEQ ID NO: 1)

NDTPASGYQVEKVVILSRHGVRAPTKMTQTMRDVTPNTWPEWPVKLGYITPRGEHLI
SLMGGFYRQKFQQQGILSQGSCPTPNSIYVWADVDQRTLKTGEAFLAGLAPQCGLTIH
HQQNLEKADPLFHPVKAGTCSMDKTQVQQAVEKEAQTPIDNLNQHYIPFLALMNTTL
NFSTSAWCQKHSADKSCDLGLSMPSKLSIKDNGNKVALDGAIGLSSTLAEIFLLEYAQ
GMPQAAWGNIHSEQEWASLLKLHNVQFDLMARTPYIARHNGTPLLQAISNALNPNAT
ESKLPDISPDNKILFIAGHDTNIANIAGMLNMRWTLPGQPDNTPPGGALVFERLADKS
GKQYVSVSMVYQTLEQLRSQTPLSLNQPAGSVQLKIPGCNDQTAEGYCPLSTFTRVVS
QSVEPGCQLQ

FIG. 1

Amino Acid Sequence of a Variant of *Buttiauxella* sp. P1-29 Phytase (SEQ ID NO: 2)

NDTPASGYQVEKVVILSRHGVRAPTKMTQTMRDVTPYTWPEWPVKLGYITPRGEHLISLMGGF
YRQKFQQQGILPQGSCPTPNSIYVWTDVAQRTLKTGEAFLAGLAPQCGLTIHHQQNLEKADPL
FHPVKAGICSMDKTQVQQAVEKEAQTPIDNLNQRYIPELALMNTVLNFSKSPWCQKHSADKPC
DLALSMPSRLSIKDNGNEVSLDGAIGLSSTLAEIFLLEYAQGMPQAAWGNIHSEQEWALLLKL
HNVYFDLMERTPYIARHKGTPLLQAISNALNPNATESKLPDISPDNKILFIAGHDTNIANIAG
MLNMRWTLPGQPDNTPPGGALVFERLADKSGKQYVSVSMVYQTLEQLRSQTPLSLNQPPGSVQ
LKIPGCNDQTAEGYCPLSTFTRVVSQSVEPGCQLQ

FIG. 2

A Nucleic Acid Sequence Encoding the Sequence of a Wild-type Buttiauxella sp. P1-29 (SEQ ID NO: 3)

AACGACACTCCCGCTTCAGGCTACCAGGTTGAGAAAGTGGTAATACTCAGCCGCCACGGGGTG
CGAGCACCAACCAAAATGACACAGACCATGCGCGACGTAACACCTAATACCTGGCCCGAATGG
CCAGTAAAATTGGGTTATATCACGCCACGCGGTGAGCATCTGATTAGCCTGATGGGCGGGTTT
TATCGCCAGAAGTTTCAACAACAGGGCATTTTATCGCAGGGCAGTTGCCCCACACCAAACTCA
ATTTATGTCTGGGCAGACGTTGATCAGCGCACGCTTAAAACTGGCGAAGCTTTCCTGGCAGGG
CTTGCTCCGGAATGTCATTTAACTATTCACCACCAGCAGGACATCAAAAAAGCCGATCCGCTG
TTCCATCCGGTGAAAGCGGGCACCTGTTCAATGGATAAAACTCAGGTCCAACAGGCCGTTGAA
AAAGAAGCTCAAACCCCCATTGATAATCTGAATCAGCACTATATTCCCTTTCTGGCCTTGATG
AATACGACCCTCAACTTTTCGACGTCGGCCTGGTGTCAGAAACACAGCGCGGATAAAAGCTGT
GATTTAGGGCTATCCATGCCGAGCAAGCTGTCGATAAAAGATAATGGCAACAAAGTCGCTCTC
GACGGGGCCATTGGCCTTTCGTCTACGCTTGCTGAAATTTTCCTGCTGGAATATGCGCAAGGG
ATGCCGCAAGCGGCGTGGGGGAATATTCATTCAGAGCAAGAGTGGGCGTCGCTACTGAAACTG
CATAACGTCCAGTTTGATTTGATGGCACGCACGCCTTATATCGCCAGACATAACGGCACGCCT
TTATTGCAGGCCATCAGCAACGCGCTGAACCCGAATGCCACCGAAAGCAAACTGCCTGATATC
TCACCTGACAATAAGATCCTGTTTATTGCCGGACACGATACCAATATTGCCAATATCGCAGGC
ATGCTCAACATGCGCTGGACGCTACCTGGGCAACCCGATAACACCCCTCCGGGCGGCGCTTTA
GTCTTTGAGCGTTTGGCCGATAAGTCAGGGAAACAATATGTTAGCGTGAGCATGGTGTATCAG
ACTCTCGAGCAGTTGCGCTCCCAAACACCACTTAGCCTTAATCAACCTGCGGGAAGCGTACAG
CTAAAAATTCCTGGCTGTAACGATCAGACGGCTGAAGGATANTGCCCGCTGTCGACGTTCACT
CGCGNGGTTAGCCAAAGCGTGGAACCAGGCTGCCAGCTACAGTAA

*FIG. 3*

Nucleic Acid Sequence of an Advantageous Variant (SEQ ID NO: 4)

```
AACGACACTCCCGCTTCAGGCTACCAGGTTGAGAAAGTGGTAATACTCAGCCGCCACGGGGTG
CGAGCACCAACCAAAATGACACAGACCATGCGCGACGTAACACCTTATACCTGGCCCGAATGG
CCAGTAAAATTGGGTTATATCACGCCACGCGGTGAGCATCTGATTAGCCTGATGGGCGGGTTT
TATCGCCAGAAGTTTCAACAACAGGGCATTTTACCGCAGGGCAGTTGCCCCACACCAAACTCA
ATTTATGTCTGGACAGACGTTGCGCAGCGCACGCTTAAAACTGGCGAAGCTTTCCTGGCAGGG
CTTGCTCCGCAATGTGGTTTAACTATTCACCACCAGCAGAATCTTGAAAAAGCCGATCCGCTG
TTCCATCCGGTGAAAGCGGGCATCTGTTCAATGGATAAAACTCAGGTCCAACAGGCCGTTGAA
AAAGAAGCTCAAACCCCCATTGATAATCTGAATCAGCGCTATATTCCCGAGCTGGCCTTGATG
AATACGGTTCTCAACTTTTCGAAATCGCCCTGGTGTCAGAAACACAGCGCGGATAAACCCTGT
GATTTAGCCCTATCCATGCCGAGCAGGCTGTCGATAAAGATAATGGCAACGAAGTCTCTCTC
GACGGGGCCATTGGCCTTTCGTCTACGCTTGCTGAAATTTTCCTGCTGGAATATGCGCAAGGG
ATGCCGCAAGCGGCGTGGGGAATATTCATTCAGAGCAAGAGTGGGCGTTGCTACTGAAACTG
CATAACGTCTATTTTGATTTGATGGAACGCACGCCTTATATCGCCAGACATAAAGGCACGCCT
TTATTGCAGGCCATCAGCAACGCGCTGAACCCGAATGCCACCGAAAGCAAACTGCCTGATATC
TCACCTGACAATAAGATCCTGTTTATTGCCGGACACGATACCAATATTGCCAATATCGCAGGC
ATGCTCAACATGCGCTGGACGCTACCTGGGCAACCCGATAACACCCCTCCGGGCGGCGCTTTA
GTCTTTGAGCGTTTGGCCGATAAGTCAGGGAAACAATATGTTAGCGTGAGCATGGTGTATCAG
ACTCTCGAGCAGTTGCGCTCCCAAACACCACTTAGCCTTAATCAACCTCCCGGAAGCGTACAG
CTAAAAATTCCTGGCTGTAACGATCAGACGGCTGAAGGATACTGCCCGCTGTCGACGTTCACT
CGCGTGGTTAGCCAAAGCGTGGAACCAGGCTGCCAGCTACAGTAA
```

*FIG. 4*

```
                              1                                          50
(SEQ ID:6) BP-110    (1)  NDTPASGYQVEKVVILSRHGVRAPTKMTQTMRDVTPYTWPEWPVKLGYIT
(SEQ ID:2) BP-112    (1)  NDTPASGYQVEKVVILSRHGVRAPTKMTQTMRDVTPYTWPEWPVKLGYIT
(SEQ ID:7) BP-111    (1)  NDTPASGYQVEKVVILSRHGVRAPTKMTQTMRDVTPYTWPEWPVKLGYIT
(SEQ ID:5) BP-17     (1)  NDTPASGYQVEKVVILSRHGVRAPTKMTQTMRDVTPNTWPEWPVKLGYIT
(SEQ ID:1)           (1)  NDTPASGYQVEKVVILSRHGVRAPTKMTQTMRDVTPNTWPEWPVKLGYIT
Buttiauxella-WT
                             51                                         100
           BP-110   (51)  PRGEHLISLMGGFYRQKFQQQGILSQSSCPTPNSIYVWTDVAQRTLKTGE
           BP-112   (51)  PRGEHLISLMGGFYRQKFQQQGILPQGSCPTPNSIYVWTDVAQRTLKTGE
           BP-111   (51)  PRGEHLISLMGGFYRQKFQQQGILPRGSCPTPNSIYVWTDVAQRTLKTGE
            BP-17   (51)  PRGEHLISLMGGFYRQKFQQQGILSQGSCPTPNSIYVWTDVAQRTLKTGE
  Buttiauxella-WT   (51)  PRGEHLISLMGGFYRQKFQQQGILSQGSCPTPNSIYVWADVDQRTLKTGE
                            101                                         150
           BP-110  (101)  AFLAGLAPQCGLTIHHQQNLEKADPLFHPVKAGICSMDKTQVQQAVEKEA
           BP-112  (101)  AFLAGLAPQCGLTIHHQQNLEKADPLFHPVKAGICSMDKTQVQQAVEKEA
           BP-111  (101)  AFLAGLAPQCGLTIHHQQNLEKADPLFHPVKAGICSMDKTQVQQAVEKEA
            BP-17  (101)  AFLAGLAPQCGLTIHHQQNLEKADPLFHPVKAGICSMDKTQVQQAVEKEA
  Buttiauxella-WT  (101)  AFLAGLAPQCGLTIHHQQNLEKADPLFHPVKAGTCSMDKTQVQQAVEKEA
                            151                                         200
           BP-110  (151)  QTPIDNLNQRYIPELALMNTVLNFSKSPWCQKHSADKPCDLALSMPSRLS
           BP-112  (151)  QTPIDNLNQRYIPELALMNTVLNFSKSPWCQKHSADKPCDLALSMPSRLS
           BP-111  (151)  QTPIDNLNQRYIPELALMNTILNFSKSPWCQKHSADKPCDLALSMPSKLS
            BP-17  (151)  QTPIDNLNQHYIPSLALMNTTLNFSKSPWCQKHSADKSCDLGLSMPSKLS
  Buttiauxella-WT  (151)  QTPIDNLNQHYIPFLALMNTTLNFSTSAWCQKHSADKSCDLGLSMPSKLS
                            201                                         250
           BP-110  (201)  IKDNGNEVSLDGAIGLSSTLAEIFLLEYAQGMPQAAWGNIHSEQEWALLL
           BP-112  (201)  IKDNGNEVSLDGAIGLSSTLAEIFLLEYAQGMPQAAWGNIHSEQEWALLL
           BP-111  (201)  IKDNGNEVSLDGAIGLSSTLAEIFLLEYAQGMPQVAWGNIHSEQEWALLL
            BP-17  (201)  IKDNGNEVSLDGAIGLSSTLAEIFLLEYAQGMPQAAWGNIHSEQEWALLL
  Buttiauxella-WT  (201)  IKDNGNKVALDGAIGLSSTLAEIFLLEYAQGMPQAAWGNIHSEQEWASLL
                            251                                         300
           BP-110  (251)  KLHNVYFDLMERTPYIARHKGTPLLQAISNALNPNATESKLPDISPDNKI
           BP-112  (251)  KLHNVYFDLMERTPYIARHKGTPLLQAISNALNPNATESKLPDISPDNKI
           BP-111  (251)  KLHNVYFDLMERTPYIARHKGTPLLQAISNALNPNATESKLPDISPDNKI
            BP-17  (251)  KLHNVYFDLMERTPYIARHKGTPLLQAISNALNPNATESKLPDISPDNKI
  Buttiauxella-WT  (251)  KLHNVQFDLMARTPYIARHNGTPLLQAISNALNPNATESKLPDISPDNKI
                            301                                         350
           BP-110  (301)  LFIAGHDTNIANIAGMLNMRWTLPGQPDNTPPGGALVFERLADKSGKQYV
           BP-112  (301)  LFIAGHDTNIANIAGMLNMRWTLPGQPDNTPPGGALVFERLADKSGKQYV
           BP-111  (301)  LFIAGHDTNIANIAGMLNMRWTLPGQPDNTPPGGALVFERLADKSGKQYV
            BP-17  (301)  LFIAGHDTNIANIAGMLNMRWTLPGQPDNTPPGGALVFERLADKSGKQYV
  Buttiauxella-WT  (301)  LFIAGHDTNIANIAGMLNMRWTLPGQPDNTPPGGALVFERLADKSGKQYV
                            351                                         400
           BP-110  (351)  SVSMVYQTLEQLRSQTPLSLNQPPGSVQLKIPGCNDQTAEGYCPLSTFTR
           BP-112  (351)  SVSMVYQTLEQLRSQTPLSLNQPPGSVQLKIPGCNDQTAEGYCPLSTFTR
           BP-111  (351)  SVSMVYQTLEQLRSQTPLSLNQPPGSVQLKIPGCNDQTAEGYCPLSTFTR
            BP-17  (351)  SVSMVYQTLEQLRSQTPLSLNQPAGSVQLKIPGCNDQTAEGYCPLSTFTR
  Buttiauxella-WT  (351)  SVSMVYQTLEQLRSQTPLSLNQPAGSVQLKIPGCNDQTAEGYCPLSTFTR
                            401       413
           BP-110  (401)  VVSQSVEPGCQLQ
           BP-112  (401)  VVSQSVEPGCQLQ
           BP-111  (401)  VVSQSVEPGCQLQ
            BP-17  (401)  VVSQSVEPGCQLQ
  Buttiauxella-WT  (401)  VVSQSVEPGCQLQ
```

BUTTIAUXELLA SP. PHYTASE VARIANTS

CROSS-REFERENCE

This application claims priority under 35 USC §371 to International Application No. PCT/US2009/041011, filed Apr. 17, 2009, which claims benefit of U.S. Provisional Patent Application No. 61/046,324, filed Apr. 18, 2008, the disclosures of which are incorporated herein by reference in their entirety for all purposes.

FIELD OF THE DISCLOSURE

The technology provided herein relates to improved variants of *Buttiauxella* sp. phytases, nucleic acids encoding the phytases, vectors, host cells containing the nucleic acids and methods for producing the phytases. The phytases encompassed by this disclosure may be used in numerous applications including, e.g., methods for starch liquefaction, alcohol fermentations and for enhancing phosphate digestion in foods and animal feeds.

BACKGROUND

Phytate is the major storage form of phosphorus in cereals and legumes. However, monogastric animals such as pig, poultry and fish are not able to metabolise or absorb phytate (or phytic acid) and therefore it is excreted, leading to phosphorous pollution in areas of intense livestock production. Moreover, phytic acid also acts as an antinutritional agent in monogastric animals by chelating metal agents such as calcium, copper and zinc.

In order to provide sufficient phosphates for growth and health of these animals, inorganic phosphate is added to their diets. Such addition can be costly and further increases pollution problems.

Through the action of phytase, phytate is generally hydrolysed to give lower inositol-phosphates and inorganic phosphate. Phytases are useful as additives to animal feeds where they improve the availability of organic phosphorus to the animal and decrease phosphate pollution of the environment (Wodzinski R J, Ullah A H. Adv Appl Microbiol. 42, 263-302 (1996)).

A number of phytases of fungal (Wyss M. et al., *Appl. Environ. Microbiol.* 65 (2), 367-373 (1999); Berka R. M. et al., *Appl. Environ. Microbiol.* 64 (11), 4423-4427 (1998); Lassen S. et al., *Appl. Environ. Microbiol.* 67 (10), 4701-4707 (2001)) and bacterial (Greiner R. et al *Arch. Biochem. Biophys.* 303 (1), 107-113 (1993); Kerovuo et al., *Appl. Environ. Microbiol.* 64 (6), 2079-2085 (1998); Kim H. W. et al., Biotechnol. Lett. 25, 1231-1234 (2003); Greiner R. et al., *Arch. Biochem. Biophys.* 341 (2), 201-206 (1997); Yoon S. J. et al., *Enzyme and microbial technol.* 18, 449-454 (1996); Zinin N. V. et al., *FEMS Microbiol. Lett.* 236, 283-290 (2004))) origin have been described in the literature.

SUMMARY OF THE DISCLOSURE

In a first aspect, embodiments of this disclosure provide phytase variants which have an amino acid sequence that varies from that of the wild type *Buttiauxella* sp. phytase (SEQ ID NO: 1), and which have one or more advantageous properties. Such properties may include but are not limited to favorable: thermostability; temperature/activity profile; pH/activity profile; specific activity; and pH/protease-sensitivity.

In a further aspect, embodiments of this disclosure relate to a phytase variant comprising a phytase that contains a substitution at one or more positions selected from the group consisting of: 75, 76 and 374, wherein each position corresponds to the position of the amino acid sequence of the wild type *Buttiauxella* sp. phytase (SEQ ID NO: 1).

In still another aspect, embodiments of this disclosure provide nucleic acids encoding phytase variants as disclosed herein, as well as vectors and host cells comprising such nucleic acids. In yet other embodiments, the sequences are employed in processes that yield the phytase variants.

Further, embodiments of this disclosure relate generally to the use of the phytase variants for liberating phosphorous from any phytase substrate, in particular inorganic phosphate from phytate or phytic acid. Advantageously, phytase variants of this disclosure may be used in industrial applications including, for example, methods for starch liquefaction and for enhancing phosphate digestion in foods and animal feeds. Advantageously, phytase variants according to embodiments of the present disclosure are useful and used in alcohol fermentations processes and/or productions.

In other aspects, this disclosure relates to enzyme compositions comprising a phytase variant as described herein, wherein the enzyme composition is useful for, or used in, commercial applications. In one embodiment, the enzyme composition may be an animal feed composition. In other embodiments, the enzyme composition may be used in starch hydrolysis (e.g. liquefaction) processes. In an advantageous embodiment, the variants and/or the enzyme composition may be used in alcohol fermentation processes. In further embodiments, an enzyme composition comprising a phytase encompassed by this disclosure will include additional enzymes, such as glucoamylases, alpha amylases, protease, cellulases, hemicellulases, lipases, pectinases, pullulanases, glucose oxidases, beta glucosidases, laccases, oxidases, cutinases, phosphatases, other phytases and combinations thereof.

In a further aspect, embodiments of this disclosure relate to methods for producing the phytase variants in a host cell by transforming the host cell with a DNA construct, advantageously including a promoter having transcriptional activity in the host cell, cultivating the transformed host cell in a suitable culture medium to allow expression of said phytase and producing the phytase. The method may also include recovering the produced phytase. In one embodiment, the host cell is a bacterial, or a plant cell, or a fungal cell (such as a *Trichoderma* cell, such as *T. reesei*) or a yeast. In embodiments described herein, the amino acid sequence of the phytase variant shares a minimum percentage sequence identity to the amino acid sequence identity with SEQ ID NO: 1, e.g., at least 80%, at least 85%, at least 90%, at least 95%, at least 96%, at least 97%, at least 98% amino acid sequence identity with SEQ ID NO: 1. In an advantageous embodiment of this disclosure, the phytase has the sequence of SEQ ID NO: 2.

The enzyme of the present invention is that defined in the claims and also herein. The enzyme of the present invention also encompasses active polypeptides that are co- or post-translationally processed during expression, for example by signal peptide cleavage. Post-translational cleavage may also occur at the C-terminal. Therefore in a preferred embodiment the effective fragment thereof (also referred to as functional fragment thereof) is the mature polypeptide produced by the native host or a suitable appropriate expression host.

Thus, in one aspect, the phytase is characterised in that it comprises an amino acid sequence that is expressed from or is expressable from all or part of the nucleotide sequence encoding the variants defined herein.

In general, in one aspect phytase variant having improved thermal activity of at least about 5° C. as compared to wild type *Buttiauxella* sp. phytase (SEQ ID NO: 1) is provided. In one embodiment the phytase the improved thermal activity is at least about 17° C. as compared to the phytase SEQ ID NO: 1. In another embodiment the improved thermal activity is in a range from about 17 to about 21° C. In a further embodiment the improved thermal activity is in a range from about 17.4 to about 20.2° C.

In general in a further aspect a thermostable phytase variant is provided that is capable of retaining greater than 50% of its activity after exposure to an elevated temperature for 10 minutes at pH 5.5 in buffer, wherein the elevated temperature is at least about 5° C. higher than a temperature at which wild type *Buttiauxella* sp. phytase (SEQ ID NO: 1) retains greater than 50% of its activity. In one aspect the elevated temperature is at least about 20.5° C. higher. In another aspect the elevated temperature is in a range from about 20.5° C. to about 27° C. In a further aspect the elevated temperature is in a range from about 20.2° C. to about 26.8° C.

In general, in another aspect a phytase variant is provided having phytase activity and an amino acid sequence that varies from the amino acid sequence of wild type *Buttiauxella* sp. phytase (SEQ ID NO: 1), wherein the amino acid sequence of the phytase variant comprises a variation at one or more positions corresponding to position 75, 76, 77, 198, 367 or 374 of SEQ ID NO: 1. In one embodiment the phytase variant further comprises one or more additional variation, wherein the variation is 92A, 164E/S, 171I/V, 192A or 256A/E/P. In another embodiment the variation at one or more of positions 75, 76, 77, 198, 367 or 374 respectively is 75P, 76R, 77S, 198R, 367L or 374P and the phytase variant further comprises one or more additional variation wherein the variation is 92A, 164E/S, 171V, 192A or 256A/E/P. In yet another embodiment the phytase variant further comprises one or more additional variation, wherein the one or more additional variation position is 26, 37, 89, 134, 160, 176, 178, 188, 190, 207, 209, 211, 235, 261, 270, 303 or 318. In a further embodiment the one or more additional variation at position 26, 37, 89, 134, 160, 176, 178, 188, 190, 207, 209, 211, 235, 261, 270, 303 or 318 is respectively 26E, 037Y, 089T, 134I/V, 160R, 176K, 178P, 188N, 190E, 207E/T, 209S, 211C, 235V, 261E, 270K, 303F or 318D. In another embodiment the phytase variant further comprises one or more additional variation, wherein the one or more additional variation position is 1, 10, 11, 38, 66, 71, 81, 92, 109, 111, 119, 120, 121, 141, 142, 152, 155, 193, 214, 239, 245, 248, 255, 268, 277, 283, 285, 287, 288, 293, 296, 314, 337, 345, 350, 364, 371, 372, 396, 399, 406 or 413. In yet another embodiment the one or more additional variation at position 1, 10, 11, 38, 66, 71, 81, 92, 109, 111, 119, 120, 121, 141, 142, 152, 155, 193, 214, 239, 245, 248, 255, 268, 277, 283, 285, 287, 288, 293, 296, 314, 337, 345, 350, 364, 371, 372, 396, 399, 406 or 413 is respectively 1S, 10I, 11I, 38S, 66E, 71K, 81A, 92E, 109Q, 111G, 119N, 120L, 121E, 141R, 142L, 152M, 155E, 193Q, 211C, 214V, 235V, 239K, 245D, 248L, 255A, 261E, 268A/T, 270K, 277T, 283D, 285K, 287D, 288A, 293G or 296S.

In general in another aspect a phytase variant is provided having phytase activity and an amino acid sequence that varies from the amino acid sequence of wild type *Buttiauxella* sp. phytase (SEQ ID NO: 1), wherein the amino acid sequence of the phytase variant comprises at least one variation as compared with SEQ ID NO: 1, and wherein the phytase sequence variation comprises a) N37Y, S75P, A89T, D92A, T134I, H160R, F164E, T171V, T176K, A178P, S188P, G192A, K198R, K207E, A209S, S248L, Q256Y, A261E, N270K, A374P
b) N37Y, G77S, A89T, D92A, T134I, H160R, F164E, T171V, T176K, A178P, S188P, G192A, K198R, K207E, A209S, S248L, Q256Y, A261E, N270K, A374P
c) N37Y, S75P, Q76R, A89T, D92A, T134I, H160R, F164E, T171I, T176K, A178P, S188P, G192A, K207E, A209S, A235V, S248L, Q256Y, A261E, N270K, A374P
d) N37Y, A89T, D92A, T134I, F164E, T171V, T176K, A178P, G192A, K207E, A209S, A235V, S248L, Q256P, A261E, N270K, A374P
e) S75P, Q76R, A89T, D92A, T134I, H160R, F164E, T171I, T176K, A178P, S188P, G192A, K207E, A209S, S248L, Q256Y, A261E, N270K, A374P
f) N37Y, Q76R, A89T, D92A, T134I, H160R, F164E, T171I, T176K, A178P, S188P, G192A, K207E, A209S, S248L, Q256Y, A261E, N270K, A374P
g) N37Y, Q76R, A89T, D92A, T134I, F164S, T171V, T176K, A178P, S188P, G192A, K207E, A209S, A235V, S248L, Q256A, A261E, N270K, A374P
h) S75P, A89T, D92A, T134I, F164E, T171V, T176K, A178P, S188P, G192A, K207E, A209S, A235V, S248L, Q256Y, A261E, N270K, A374P
i) S75P, Q76R, A89T, D92A, T134I, H160R, F164E, T171V, T176K, A178P, S188P, G192A, K207E, A209S, A235V, S248L, Q256Y, A261E, N270K, P367L, A374P
j) N37Y, A89T, D92A, T134I, F164E, T171I, T176K, A178P, G192A, K207E, A209S, A235V, S248L, Q256Y, A261E, N270K, A374P
k) N37Y, Q76R, A89T, D92A, T134I, F164E, T171V, T176K, A178P, G192A, K207E, A209S, S248L, Q256Y, A261E, N270K, A374P
l) N37Y, Q76R, A89T, D92A, T134I, F164E, T171V, T176K, A178P, G192A, K207E, A209S, S248L, Q256A, A261E, N270K, A374P
m) N37Y, S75P, Q76R, A89T, D92A, T134I, F164E, T171V, T176K, A178P, K207E, A209S, A235V, S248L, Q256A, A261E, N270K, A374P
n) N37Y, S75P, A89T, D92A, T134I, H160R, F164E, T171V, T176K, A178P, K207E, A209S, A235V, S248L, Q256Y, A261E, N270K, A374P
o) N37Y, A89T, D92A, T134I, H160R, F164S, T171I, T176K, A178P, S188P, G192A, K207E, A209S, A235V, S248L, Q256E, A261E, N270K, A374P
p) A89T, D92A, T134I, H160R, F164E, T171V, T176K, A178P, G192A, K207E, A209S, A235V, S248L, Q256Y, A261E, N270K, A374P
q) N37Y, S75P, A89T, D92A, T134I, H160R, F164S, T171V, T176K, A178P, S188P, K207E, A209S, S248L, Q256H, A261E, N270K, A374P
r) N37Y, S75P, A89T, D92A, T134I, F164S, T171V, T176K, A178P, S188P, G192A, K207E, A209S, S248L, Q256A, A261E, N270K, A374P
s) S75P, Q76R, A89T, D92A, T134I, H160R, F164E, T171V, T176K, A178P, G192A, K207E, A209S, S248L, Q256A, A261E, N270K, A374P; or
t) N37Y, Q76R, A89T, D92A, T134I, H160R, F164S, T171V, T176K, A178P, G192A, K207E, A209S, A235V, S248L, Q256Y, A261E, N270K, A374P.

In one embodiment the phytase sequence variation comprises N37Y, S75P, Q76R, A89T, D92A, T134I, H160R, F164E, T171I, T176K, A178P, S188P, G192A, K207E, A209S, A235V, S248L, Q256Y, A261E, N270K, A374P.

Also provided is a phytase which has at least a minimum percent sequence identity and/or percent homology to the phytase(s) disclosed herein, wherein the minimum percent identity and/or homology is at least 50%, at least 60%, at least 75%, at least 80%, at least 85%, at least 90%, at least 93%, at least 95%, at least 96%, at least 97%, at least 98% or at least 99%.

In general in one aspect a phytase variant is provided having phytase activity and an amino acid sequence that varies from the amino acid sequence of the wild type *Buttiauxella* sp. phytase (SEQ ID NO: 1), wherein the amino acid sequence of the phytase variant comprises at least one variation as compared with SEQ ID NO: 1, and wherein the variant has a variation at at least any one of the following positions: 70, 193, 197, 221 and 407. In one embodiment the variant has at least the following variations: N70Y, H193R, F197E, S221P and A407P.

In general, in another aspect a nucleic acid encoding any of the phytase(s) disclosed herein is provided. In another aspect, a vector comprising the nucleic acid encoding any of the phytase(s) disclosed herein is provided. In a further aspect a host cell comprising the nucleic acid and/or the vectors described herein are provided.

In general, in another aspect a method of producing a phytase variant according to the variants disclosed herein, in a host cell is provided, comprising
a) transforming a host cell with a DNA construct comprising the nucleic acid encoding any of the phytase variants disclosed herein, and
b) cultivating the transformed host cell in a suitable culture medium.

In one embodiment the host cell is a fungal cell, a bacterial cell or a plant cell.

In one aspect a phytase prepared by the methods disclosed herein is provided.

In general, in one aspect an enzyme composition comprising at least one phytase as disclosed herein including additionally one or more of a glucoamylase, an alpha-amylase, a protease, a pullulanase, an isoamylase, a cellulase, a hemicellulase, a xylanase, a cyclodextrin glycotransferase, a lipase, a laccase, an oxidase, an esterase, a cutinase, another phytase or any combinations thereof. In one embodiment the composition additionally includes an alpha-amylase.

In general, in another aspect the use of a phytase as described herein or an enzyme composition as described herein, in starch liquefaction, saccharification, fermentation or simultaneous saccharification-fermentation is provided. In one embodiment the starch liquefaction, saccharification, fermentation or simultaneous saccharification-fermentation is for production of fermentation alcohol. In another embodiment the alcohol is ethanol or butanol. In yet another embodiment a substrate is subjected to the starch liquefaction, saccharification, fermentation or simultaneous saccharification-fermentation. In one embodiment the substrate comprises starch. In another embodiment the substrate comprises a grain or cereal. In a further embodiment the grain or cereal is wheat, barley, rye, oats, maize, sorghum, corn gluten meal, Distillers Dried Grain Solubles (DDGS), wheat bran, wheat middlings, wheat shorts, rice, oat hulls, palm kernel, citrus pulp or combinations thereof. In one embodiment the rice comprises rice bran or rice hulls.

In general, in another aspect the use of at least one phytase as disclosed herein as an additive to a food or feed is provided. In another aspect the use of at least one phytase as disclosed herein as an additive to a food or feed containing Distillers Dried Grain Solubles (DDGS).

In general, in a further aspect a method for production of food or animal feed is provided comprising a step of admixing at least one phytase as disclosed herein or an enzyme composition as disclosed herein with another food or feed ingredient to form said food or animal feed.

In general, another aspect a method for production of food or animal feed is provided comprising a step of spraying at least one phytase as disclosed herein or an enzyme composition as disclosed herein in liquid form onto said food or animal feed. In one aspect, a method for production of food or animal feed comprising a step of mixing at least one phytase as disclosed herein or an enzyme composition as disclosed herein as a dry product with said food or animal feed.

In another aspect a method for production of animal feed is provided comprising a step of admixing at least one phytase as disclosed herein or an enzyme composition as disclosed herein with another food or feed ingredient to form said animal feed. In a further aspect a method for production of animal feed is provided comprising a step of spraying at least one phytase as disclosed herein or an enzyme composition as disclosed herein in liquid form onto said animal feed. In one more aspect a method for production of animal feed is provided comprising a step of mixing at least one phytase as disclosed herein or an enzyme composition as disclosed herein as a dry product with said animal feed.

In general, in another aspect a food or animal feed composition is provided comprising either i) at least one phytase as disclosed herein or an enzyme composition as disclosed herein and/or ii) a food or animal feed produced by the method as disclosed herein. In a further aspect an animal feed composition is provided comprising either i) at least one phytase as disclosed herein or an enzyme composition as disclosed herein and/or ii) a food or animal feed produced by the method as disclosed herein.

In one aspect a use of at least one phytase as disclosed herein or an enzyme composition as disclosed herein in food or animal feed is provided. In another aspect, a use of at least one phytase as disclosed herein or an enzyme composition as disclosed herein in an animal feed is provided.

In general, in another aspect a method of reducing the levels of phosphorus in animal manure is provided, characterized in that an animal is fed with at least one phytase as disclosed herein or an enzyme composition as disclosed herein or a feed prepared by the method as disclosed herein or a composition as disclosed herein, and wherein said phytase is in an amount effective in converting phytate contained in said animal feed.

In general, in one aspect a use of at least one phytase as disclosed herein or an enzyme composition as disclosed herein or a feed prepared by the method as disclosed herein or a composition as disclosed herein, in the manufacture of an animal feed to reduce the levels of phosphorus in manure from the animal fed with said phytase polypeptide is provided.

BRIEF DESCRIPTION OF THE DRAWINGS

FIG. 1. shows the amino acid sequence of a wild-type *Buttiauxella* sp. P1-29 phytase, ("BP-WT"), (SEQ ID NO: 1).

FIG. 2. shows the amino acid sequence of one advantageous variant according to the present disclosure (SEQ ID NO: 2).

FIG. 3. shows the nucleic acid sequence of a wild-type *Buttiauxella* sp. P1-29 (SEQ ID NO: 3).

FIG. 4. shows the nucleic acid sequence of an advantageous variant according to the present disclosure shown in FIG. 2 (SEQ ID NO: 4).

FIG. 5 presents the amino acid sequences for three enzymes according to the present invention (BP 110, BP-111 and BP-112), as well as the sequences for BP-17 and the wt sequence.

DETAILED DESCRIPTION OF THIS DISCLOSURE

Figure 6A:
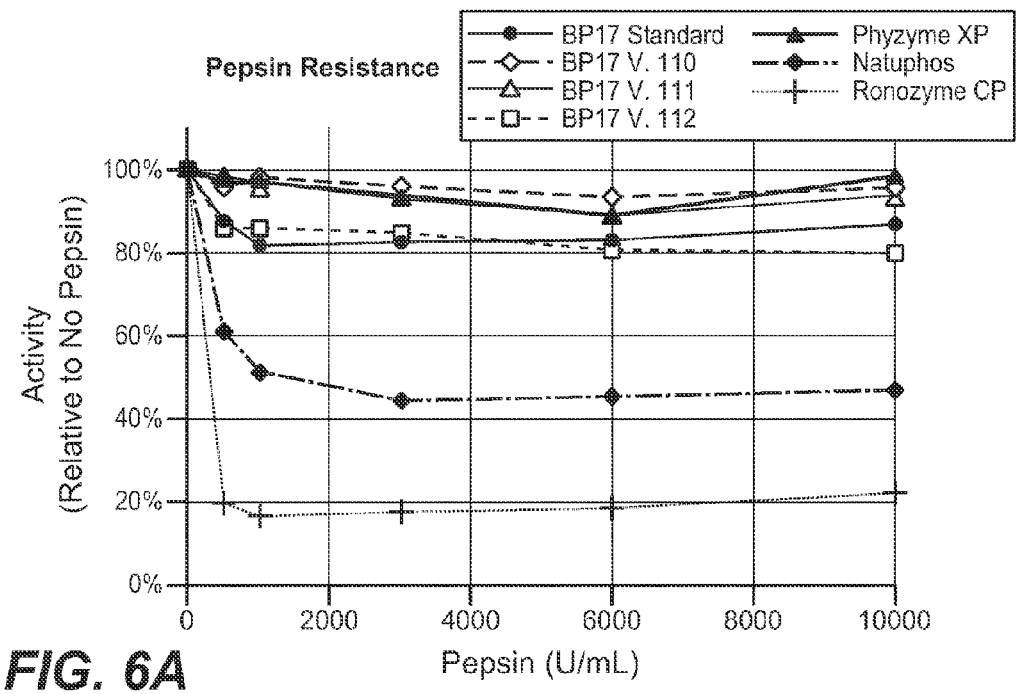
FIG. 6 shows the resistance of the phytases originating from *Buttiauxella*, variants BP-17, BP-110, BP-111, and BP-112, and of Phyzyme XP, Natuphos, and Ronozyme P against increasing concentrations of pepsin. Data are relative to incubation at pH 2 without pepsin. A: all data points, B: same data but showing only more than 70% recovery.

Disclosed herein are variants of *Buttiauxella* sp. phytases that may be used in industrial applications including methods for starch liquefaction, alcohol fermentations and for enhancing phosphate digestion in foods and animal feeds. In particular, phytase variants according to the present disclosure are very useful for phytate degradation in starch liquefaction steps in fuel ethanol production processes. The variants of this disclosure comprise one or more variations (including substitutions, insertions and deletions) from the amino acid sequence of the wild type *Buttiauxella* sp. phytase (SEQ ID NO: 1). In an advantageous embodiment, the amino acid sequence of the variant comprises at least one variation as compared to the amino acid sequence of SEQ. ID NO: 1, and the at least one variation is at one, two or three positions selected from the group consisting of: 75, 76 and 374, wherein each position corresponds to the position of the amino acid sequence of SEQ ID NO: 1.

For example, advantageously the variation in the phytase variants according to embodiments of the present disclosure is selected from the group consisting of: S75, Q76 and A374 corresponding to SEQ ID NO: 1.

In advantageous embodiments of the present disclosure, the variation in the phytase variant is a substitution and the substitution can be selected from the group consisting of: S75P, Q76R and A374P wherein each position corresponds to the position of the amino acid sequence of SEQ ID NO: 1.

In further advantageous embodiments, phytase variants according to the present disclosure comprises a further variation at one or more positions selected from the group consisting of: N37, G77, H160, F164, T171, S188, G192, K198, A235, Q256 and/or P367 wherein each position corresponds to the position of the amino acid sequence of SEQ ID NO: 1.

In yet other advantageous embodiments, the variation in phytase variants according to the present disclosure is a substitution and the substitution can be at one or more positions selected from the group consisting of: N37Y, G77S, H160R, F164E, F164S, T171V, T171I, S188P, G192A, K198R, A235V, Q256P, Q256A, Q256E and/or P367L.

In other advantageous embodiments, phytase variants according to the present disclosure comprises further a variation at one or more positions consisting of: A89, D92, T134, F164, T176, A178, K207, A209, S248, Q256, A26E and/or N270.

Further, in other advantageous embodiments, phytase variants according to the present disclosure comprises a further variation at one or more positions selected from the group consisting of: A89T, D92A, T134I, F164S, T176K, A178P, K207E, A209S, S248L, Q256Y, A261E and/or N270K.

In yet other advantageous embodiments, phytase variants according to the present disclosure comprises a sequence of SEQ ID NO: 2.

Advantageous phytase variants according to the present disclosure comprises a sequence containing variations selected from the group consisting of:

a) N37Y, S75P, A89T, D92A, T134I, H160R, F164E, T171V, T176K, A178P, S188P, G192A, K198R, K207E, A209S, S248L, Q256Y, A261E, N270K, A374P b) N37Y, G77S, A89T, D92A, T134I, H160R, F164E, T171V, T176K, A178P, S188P, G192A, K198R, K207E, A209S, S248L, Q256Y, A261E, N270K, A374P c) N37Y, S75P, Q76R, A89T, D92A, T134I, H160R, F164E, T171I, T176K, A178P, S188P, G192A, K207E, A209S, A235V, S248L, Q256Y, A261E, N270K, A374P d) N37Y, A89T, D92A, T134I, F164E, T171V, T176K, A178P, G192A, K207E, A209S, A235V, S248L, Q256P, A261E, N270K, A374P e) S75P, Q76R, A89T, D92A, T134I, H160R, F164E, T171I, T176K, A178P, S188P, G192A, K207E, A209S, S248L, Q256Y, A261E, N270K, A374P f) N37Y, Q76R, A89T, D92A, T134I, H160R, F164E, T171I, T176K, A178P, S188P, G192A, K207E, A209S, S248L, Q256Y, A261E, N270K, A374P g) N37Y, Q76R, A89T, D92A, T134I, F164S, T171V, T176K, A178P, S188P, G192A, K207E, A209S, A235V, S248L, Q256A, A261E, N270K, A374P h) S75P, A89T, D92A, T134I, F164E, T171V, T176K, A178P, S188P, G192A, K207E, A209S, A235V, S248L, Q256Y, A261E, N270K, A374P i) S75P, Q76R, A89T, D92A, T134I, H160R, F164E, T171V, T176K, A178P, S188P, G192A, K207E, A209S, A235V, S248L, Q256Y, A261E, N270K, P367L, A374P j) N37Y, A89T, D92A, T134I, F164E, T171I, T176K, A178P, G192A, K207E, A209S, A235V, S248L, Q256Y, A261E, N270K, A374P k) N37Y, Q76R, A89T, D92A, T134I, F164E, T171V, T176K, A178P, G192A, K207E, A209S, S248L, Q256Y, A261E, N270K, A374P l) N37Y, Q76R, A89T, D92A, T134I, F164E, T171V, T176K, A178P, G192A, K207E, A209S, S248L, Q256A, A261E, N270K, A374P m) N37Y, S75P, Q76R, A89T, D92A, T134I, F164E, T171V, T176K, A178P, K207E, A209S, A235V, S248L, Q256A, A261E, N270K, A374P n) N37Y, S75P, A89T, D92A, T134I, H160R, F164E, T171V, T176K, A178P, K207E, A209S, A235V, S248L, Q256Y, A261E, N270K, A374P o) N37Y, A89T, D92A, T134I, H160R, F164S, T171I, T176K, A178P, S188P, G192A, K207E, A209S, A235V, S248L, Q256E, A261E, N270K, A374P p) A89T, D92A, T134I, H160R, F164E, T171V, T176K, A178P, G192A, K207E, A209S, A235V, S248L, Q256Y, A261E, N270K, A374P q) N37Y, S75P, A89T, D92A, T134I, H160R, F164S, T171V, T176K, A178P, S188P, K207E, A209S, S248L, Q256H, A261E, N270K, A374P r) N37Y, S75P, A89T, D92A, T134I, F164S, T171V, T176K, A178P, S188P, G192A, K207E, A209S, S248L, Q256A, A261E, N270K, A374P s) S75P, Q76R, A89T, D92A, T134I, H160R, F164E, T171V, T176K, A178P, G192A, K207E, A209S, S248L, Q256A, A261E, N270K, A374P t) N37Y, Q76R, A89T, D92A, T134I, H160R, F164S, T171V, T176K, A178P, G192A, K207E, A209S, A235V, S248L, Q256Y, A261E, N270K, A374P.

Embodiments of this disclosure also include variants of any of the phytases set forth in sequences a) to t), which have phytase activity and an amino acid sequence having a percent sequence identity and/or percent homology of at least 50%, at least 60%, at least 75%, at least 80%, at least 85%, at least 90%, at least 93%, at least 95%, at least 96%, at least 97%, at least 98%, and at least 99% as compared to each of the phytase variants set forth in sequences a) to t).

Amino acids are referred to herein using the name of the amino acid, the three letter abbreviation or the single letter abbreviation. The table below provides a list of the standard amino acids together with their abbreviations.

| Alanine | A | Ala |
| Cysteine | C | Cys |
| Aspartic acid | D | Asp |
| Glutamic acid | E | Glu |
| Phenylalanine | F | Phe |
| Glycine | G | Gly |
| Histidine | H | His |
| Isoleucine | I | Ile |
| Lysine | K | Lys |
| Leucine | L | Leu |
| Methionine | M | Met |
| Asparagine | N | Asn |
| Proline | P | Pro |
| Glutamine | Q | Gln |
| Arginine | R | Arg |
| Serine | S | Ser |
| Threonine | T | Thr |
| Valine | V | Val |
| Tryptophan | W | Trp |
| Tyrosine | Y | Tyr |
| Cysteine | C | Cys |
| Aspartic acid | D | Asp |

In addition to the specific amino acid variations and nucleic acids encoding the variations, conservative amino acid substitutions of the variations are provided herein. Such substitutions are those which are conservative, for example, wherein the variant amino acid is replaced by another amino acid of the same general type Amino acids can be classified as acidic, basic, neutral and polar, or neutral and nonpolar and/or aromatic, depending on their side chain. Preferred substitutions of a variant amino acid position include those that have one or more classifications that are the same as the variant amino acid at that position. Thus, in general, amino acids Lys, Arg, and His are basic; amino acids aspartic and glutamic are acidic; amino acids Ser, Thr, Cys, Gln, and Asn are neutral polar; amino acids Gly, Ala, Val, Ile, and Leu are nonpolar aliphatic, and amino acids Phe, Trp, and Tyr are aromatic. Gly and Ala are small amino acids and Val, Ile and Leu are alipathic amino acids.

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Phytic acid (myo-inositol hexakisphosphate) is an important constituent in cereals, legumes and oilseed crops. The salt form, phytate, is the major storage form of phosphorous in these plants.

Phytases catalyse phosphate monoester hydrolysis of phytic acid which results in the step-wise formation of myo-inositol pentakis-, tetrakis-, tris-, bis- and monophosphates, as well as the liberation of inorganic phosphate.

The terms "phytase variant" or "variant" or "modified form" refer to a phytase enzyme with an amino acid sequence derived from the amino acid sequence of a parent phytase having one or more amino acid substitutions, insertions, and/or deletions, which together are referred to as "mutations".

The terms "parent phytase" or "parent enzyme" refer to a phytase enzyme from which a phytase variant is derived. A parent phytase can be a wild type phytase or another phytase variant. In particular, in the present invention, a "parent phytase" may be derived from a *Buttiauxella* sp. Suitably, the "parent phytase" is derived from *Buttiauxella* strain P1-29 as described herein which, preferably has the amino acid sequence set out herein.

As used herein, the term "phytase" or "phytase activity" refers to a protein or polypeptide which is capable of catalyzing the hydrolysis of phytate to (1) myo-inositol and/or (2) mono-, di-, tri-, tetra- and/or penta-phosphates thereof and (3) inorganic phosphate. For example, enzymes having catalytic activity as defined in Enzyme Commission EC number 3.1.3.8 or EC number 3.1.3.26.

The term "a *Buttiauxella* sp. phytase", as used herein refers to a phytase protein obtained from a *Buttiauxella* sp. In one embodiment, the *Buttiauxella* sp. phytase comprises the amino acid sequence derived from a strain deposited under the accession number NCIMB 41248 (National Collections of Industrial Marine and Food Bacteria, Scotland, UK). In one advantageous embodiment, a *Buttiauxella* sp. phytase comprises the amino acid sequence of SEQ ID NO: 2.

The term "corresponding to a *Buttiauxella* sp. phytase", as used herein, refers to an enzyme having one or more of the same or similar functional characteristics or sequence of a *Buttiauxella* sp. phytase, but not necessarily obtained from a source of *Buttiauxella* sp.

The term "*Buttiauxella*" refers to a genus of gram negative, facultatively anaerobic bacteria of the family Enterobacteriaceae and *Buttiauxella* spp include *B. agrestis*, *B. brennerase*, *B. ferragutiae*, *B. gaviniae*, *B. izardii*, *B. noackiae*, and *B. warmboldiae*.

Strains of the *Buttiauxella* species are available for example from the American Type Culture Collection (ATCC) and DSMZ, the German National Resource Centre for Biological Material.

The term "wild-type phytase" or "wild-type" refers to an enzyme with an amino acid sequence found in nature. In particular, the wild-type phytase is that shown as SEQ ID. No. 1.

The term "variant" of *Buttiauxella* sp. phytase" or "phytase variant" as used herein means a phytase enzyme with an amino acid sequence that differs by at least one amino acid substitution, insertion and/or deletion as compared with the amino acid sequence of the phytase of SEQ. ID NO: 1. The terms "variant" and "variation" as used herein merely means that there is a difference between sequence of the amino acid sequence of the phytase variant and the amino acid sequence of SEQ. ID NO: 1, and does not mean that an amino acid sequence or nucleotide sequence of SEQ. ID NO: 1 or any other phytase served as a starting material in any way and/or was physically varied, mutated, modified or otherwise altered to yield the variant. Simply put, the phytase variants of this disclosure (including their amino acid and nucleotides sequences), may be prepared by any method, and skilled artisans will be readily familiar with numerous methods, some of which are described herein, for making the phytase variants.

The term "protein", as used herein, includes proteins, polypeptides, and peptides.

The terms "amino acid residue equivalent to", "amino acid corresponding to" and grammatical equivalents thereof are used herein to refer to an amino acid residue of a protein having the similar position and effect as that indicated in a particular amino acid sequence of a particular protein. The person of skill in the art will recognize the equivalence of specified residues in comparable phytase proteins.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff et., Suppl. 3:353-358, National Biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information. Likewise, computer programs for determining percent homology are also readily available.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, temperature and/or pH activity profile, feed processing stability, and ability to be secreted.

The term "enhanced stability" in the context of a property such as stability at higher temperatures, lower pH, etc. refers to a higher retained enzyme activity over time as compared to another identified phytase such as that of SEQ ID NO: 1. Unless another phytase is specifically identified, the term "enhanced stability" when used herein, will refer to a higher retained enzyme activity over time as compared to the phytase of SEQ ID NO: 1.

The terms "thermally stable" and "thermostable" refer to phytases of the present disclosure that retain a specified amount of enzymatic activity after exposure to an elevated temperature. Phytase variants according to this disclosure are considered thermostable at a specified temperature if the enzyme retains greater than 50% of its activity after exposure to the specified temperature for 10 minutes at pH 5.5 in buffer.

The term "improved thermal activity" as it pertains to phytase variants of the present disclosure means that the phytase variant exhibits the same or an increased amount of phytase enzyme activity at elevated temperature as compared to the phytase enzyme activity of another identified phytase such as that of SEQ ID NO: 1. Unless another phytase is specifically identified, the term "improved thermal activity" when used herein will refer to the thermal activity of a phytase variant of this disclosure as compared to the thermal activity of the phytase of SEQ ID NO: 1. Further discussion about thermal activity is provided below in Example 6.

The terms "polynucleotide" and "nucleic acid", used interchangeably herein, refers to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases.

As used herein the term "gene" refers to a polynucleotide (e.g., a DNA segment), that encodes a polypeptide and includes regions preceding and following the coding regions as well as intervening sequences (introns) between individual coding segments (exons).

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In preferred embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes and the like.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "optimal alignment" refers to the alignment giving the highest percent identity score.

The terms "protein" and "polypeptide" are used interchangeability herein. In the present disclosure and claims, the conventional one-letter and three-letter codes for amino acid residues are used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Variants of this disclosure are described by the following nomenclature: [original amino acid residue of SEQ. ID NO: 1/position of original amino acid residue in SEQ. ID NO: 1/substituted amino acid residue]. For example, in SEQ ID NO: 2, the substitution of threonine (T) for the original alanine (A) in position 89 of SEQ ID NO: 1 is represented as A89T. When a position suitable for substitution is identified herein without a specific amino acid suggested, it is to be understood that any amino acid residue may be substituted for the amino acid residue present in the position. Where a variant phytase contains a deletion in comparison with other phytases the deletion is indicated with "*". For example, a deletion at position A89 of SEQ. ID NO: 1 is represented as A89*. A deletion of two or more consecutive amino acids is indicated, for example, as (89-91)*.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein.

"Host strain" or "host cell" refers to a suitable host for an expression vector comprising DNA according to the present disclosure.

The terms "derived from" and "obtained from" refer to not only a phytase produced or producible by a strain of the organism in question, but also a phytase encoded by a DNA sequence isolated from such strain and produced in a host organism containing such DNA sequence. Additionally, the terms refers to a phytase which is encoded by a DNA sequence of synthetic and/or cDNA origin and which has the identifying characteristics of the phytase in question. Hence, a phytase that is "derived from" and "obtained from" another phytase does not necessarily mean that the phytase has been physically derived or physically obtained from the second phytase, but rather can also mean that the phytase in question has been prepared using knowledge or ideas derived from knowledge of the second phytase.

By "functional fragment" is meant a fragment of the polypeptide that retains that characteristic properties of that polypeptide. In the context of the present invention, a functional fragment of a phytase enzyme is a fragment that retains the phytase cleavage capability of the whole protein.

The term "isolated", "recovered" or "purified" refers to a material that is removed from its original environment. The term "substantially purified" means that the material has been purified to at least a substantial degree.

In one aspect, preferably the nucleotide or amino acid sequence is in an isolated form. The term "isolated" means that the sequence is at least substantially free from at least one other component with which the sequence is naturally associated in nature and as found in nature.

In one aspect, preferably the nucleotide or amino acid sequence is in a purified form. The term "purified" means that the sequence is in a relatively pure state at least 1%, 5% pure or 10% pure, more preferably at least 20%, 30%, 40%, 50%, 60%, 70%, 80%, 90% pure. In a preferred embodiment, when referring to a polypeptide, the purity as defined above is determined in terms of being purified from other polypeptides by SDS-PAGE electrophoresis. In a preferred embodiment, when referring to a polynucleotide, the purity as defined above is determined in terms of being purified from other polynucleotides.

As used with reference to the present invention, the terms "expression", "expresses", "expressed" and "expressable" are synonymous with the respective terms "transcription", "transcribes", "transcribed" and "transcribable".

As used with reference to the present invention, the terms "transformation" and "transfection" refer to a method of introducing nucleic acid sequences into hosts, host cells, tissues or organs.

As used with reference to the present invention, the terms "produce", "producing", "produced", "produceable", "production" are synonymous with the respective terms "prepare", "preparing", "prepared", "preparation", "generated", "generation" and "preparable".

A "feed" and a "food," respectively, means any natural or artificial diet, meal or the like or components of such meals intended or suitable for being eaten, taken in, digested, by an animal (feed) and a human being (food), respectively.

A "food or feed additive" is a compound or a multi component composition intended for or suitable for being added to food or feed. It may, but is not required to, comprise one or more compounds such as vitamins, minerals or feed enhancing enzymes and suitable carriers and/or excipients, and it is usually provided in a form that is suitable for being added to animal feed.

The term "starch liquefaction" refers to a process by which starch is converted to shorter chain and less viscous dextrins.

The term "substrate" refers to a substance that is or comprises at least one entity that can be acted on by the enzyme(s) of the present invention. Examples of such entities include: phytate, and intermediate products of phytate degradation such as inositol pentaphosphates, tetraphosphates, triphosphates diphosphates, and monophosphates. Examples of substrates that comprise said entity include grains, cereals and other plant materials or carbohydrate-based materials for use in, for example, ingredients for feeds, liquefaction, saccharification, fermentation, simultaneous saccharification/fermentation and/or single step process for production of, for example, fermentation alcohols (e.g., ethanol or butanol) or sugars for use in fermentations for the production of alcohols (e.g., ethanol or butanol) or sugars for making other products (e.g., non-alcohol products).

The term "alcohol fermentations" refers to fermentative processes in which a microorganism (e.g., a yeast) converts a substrate into a metabolite which is classified as an alcohol (e.g., ethanol or butanol).

A "promoter" is a regulatory sequence that is involved in binding RNA polymerase to initiate transcription of a gene.

"Under transcriptional control" is a term well understood in the art to indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein when describing proteins and genes that encode them, the term for the gene is italicized, (e.g., the gene that encodes *Buttiauxella* phytase). The term for the protein is generally not italicized and the first letter is generally capitalized.

The term "operably linked" refers to juxtaposition wherein the elements are in an arrangement allowing them to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The terms "recovered", "isolated", and "separated" as used herein refer to a compound, protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

Although any methods and materials similar or equivalent to those described herein can be used in the practice or testing of the present disclosure, exemplary and advantageous methods and materials are now described. All publications mentioned herein are incorporated herein by reference to the extent necessary to disclose and describe the methods and/or materials connected with the disclosure for which the publications are cited.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Phytase enzymes used as parent or precursor enzymes include a *Buttiauxella* sp. phytase and those enzymes corresponding to a *Buttiauxella* sp. phytase. In some embodiments, the parent *Buttiauxella* sp. phytase comprises the amino acid sequence derived from a *Buttiauxella* sp. strain deposited under the accession number NCIMB 41248. In some embodiments, the parent *Buttiauxella* sp. phytase comprises the amino acid sequence of SEQ ID NO: 1. In some embodiments, the parent *Buttiauxella* sp. phytase is derived from *B. agrestis, B. brennerase, B. ferragutiae, B. gaviniae, B. izardii, B. noackiae,* and *B. warmboldiae*. Reference is made to WO 2006/043178, which is specifically incorporated herein by reference and which describes phytases obtainable from or derived from a parent *Buttiauxella* sp. and phytases corresponding to a *Buttiauxella* sp. phytase enzyme. In some embodiments, a wild-type *Buttiauxella* sp. Phytase variant has at least 50%, at least 60%, at least 75%, at least 80%, at least 85%, at least 90%, at least 93%, at least 95%, at least 96%, at least 97%, at least 98%, and at least 99% amino acid sequence identity to the polypeptide of SEQ ID NO: 1.

Embodiments of the present disclosure are concerned with variant phytases (e.g., variant *Buttiauxella* sp. phytases). Specifically, WO 2006/043178 describes the mutagenesis of a wild-type phytase enzyme having the sequence disclosed therein as SEQ ID NO: 3. A number of preferred mutations are taught in WO 2006/043178. A variant phytase will contain at least one amino acid substitution, deletion or insertion, with amino acid substitutions often being advantageous. The amino acid substitution, insertion or deletion may occur at any residue within the phytase peptide. A phytase variant of the present disclosure is a variant which does not have an amino acid sequence identical to the amino acid sequence of SEQ ID NO: 1 herein.

In advantageous embodiments of the present disclosure, the variant will comprise a substitution in a *Buttiauxella* sp. phytase and more specifically corresponding to said equivalent positions in SEQ ID NO: 1. In some embodiments, the substitution comprises any of the remaining 19 amino acids corresponding to A, C, D, E, F, 0, H, I, K, L, M, N, P, Q, R, S, T, V, W or Y. However, also synthetic and other amino acids could be used.

Variants may be prepared by random mutagenesis, site saturation mutagenesis, and site specific mutagenesis of nucleotides in the DNA encoding the phytase protein, using cassette or PCR mutagenesis or other techniques well known in the art, to produce variants, which may thereafter be produced in cell culture. Reference is made to Morinaga et al., (1984) *Biotechnology* 2: 646-649; Nelson and Long, (1989) *Analytical Biochem.*, 180: 147-151 and Sarkar and Sommer (1999) *Biotechniques* 8: 404-407. Variant phytase protein fragments may also be prepared by in vitro synthesis using established techniques.

Polynucleotides may be obtained by standard procedures known in the art from, for example, cloned DNA (e.g., a DNA "library"), by chemical synthesis, by cDNA cloning, by PCR (U.S. Pat. No. 4,683,202 or Saiki et al., *Science* 239:487-491 (1988)), by synthetically established methods (Beucage et al., (1981) Tetrahedron Letters 22: 1859-1869 and Matthes et al, *EMBO J.* 3:801-895(1984)) or by the cloning of genomic DNA, or fragments thereof, substantially purified from a desired cell, such as a *Buttiauxella* sp. (see, for example, Sambrook et al., 2001, Molecular Cloning, A Laboratory Manual, 3d Ed., Cold Spring Harbor Laboratory Press, Cold Spring Harbor, N.Y.; Glover, D M and Hames, B D (Eds.), 1995, DNA Cloning 1: A Practical Approach and DNA Cloning 2: A Practical Approach, Oxford University Press, Oxford). Nucleic acid sequences derived from genomic DNA, and derivatives thereof, may contain regulatory regions in addition to coding regions.

To express the polypeptides standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. It is understood that the design of the expression vector, including the selection of regulatory sequences is affected by factors such as the choice of the host cell, the level of expression of protein desired and whether expression is constitutive or inducible.

Transfection of the expression vector into a host cell can be carried out using standard techniques such as electroporation, calcium-phosphate precipitation, and DEAE-dextran transfection.

Suitable host cells for cloning or expressing the DNA in the vectors herein are the prokaryote, yeast, or higher eukaryote cells like plant cells as described above. In addition to prokaryotes, eukaryotic microbes such as filamentous fungi or yeast are suitable cloning or expression hosts for the phytase variants according to this disclosure.

Host cells can be transformed with the above-described expression or cloning vectors for protein production and cultured in conventional nutrient media modified as appropriate for inducing promoters, selecting transformants, or amplifying the genes encoding the desired sequences. The culture conditions, such as temperature, pH, and the like, are those previously used with the host cell selected for expression, and will be apparent to the ordinarily skilled artisan.

The polypeptide prepared from the cells can be purified using, for example, hydroxylapatite chromatography, gel electrophoresis, dialysis, and affinity chromatography.

In some embodiments, a variant phytase according to this disclosure will have altered properties. Advantageously, a variant according to embodiments of this disclosure will have improved properties as compared to the wild type phytase of SEQ. ID NO: 1. In some embodiments, the altered, e.g., improved properties will be thermal stability, thermal activity, feed processing stability and/or specific activity (see FIG. 2).

In some embodiments, variants encompassed by this disclosure will have increased thermal stability as compared to *Buttiauxella* sp. phytases known in the art (e.g., *Buttiauxella* sp. phytases according to SEQ ID NO: 1). In some embodiments, the variant will have a thermal stability difference (TD) of at least 21.9° C., at least 22.4° C., at least 22.6° C., at least 22.9° C., at least 23.2° C., at least 23.4° C., at least 23.5° C., at least 23.5° C., at least 23.7° C., at least 24.1° C., at least 24.2° C., at least 24.4° C., at least 24.9° C., at least 25.0° C., at least 25.9° C., at least 26.5° C. and at least 26.8° C. compared to BP-WT.

In some embodiments, variants encompassed by this disclosure will exhibit increased stability at elevated temperatures as compared to the wild type phytase of SEQ. ID NO: 1. In some embodiments, the phytase variant will be thermostable at about 65° C., at about 70° C., at about 75° C., at about 80° C. or higher. As discussed above, phytases according to this disclosure are considered thermo stable if the enzyme retains greater than 50% of its activity after exposure to a specified temperature for 10 minutes at pH 5.5.

In some embodiments, variants will have a higher thermal activity. In some embodiments, the variant encompassed by this disclosure will have a thermal activity difference (TAD) of at least 17.4° C., at least 17.5° C., at least 17.6° C., at least 17.8° C., at least 17.9° C., at least 18.4° C., at least 18.7° C., at least 18.8° C., at least 18.9° C., at least 19.0° C., at least 19.3° C., at least 19.5° C., at least 20.0° C., at least 20.1° C. and at least 20.2° C. compared to BP-WT.

In some embodiments, variant phytases according to this disclosure will have a specific activity of at least 1000 U/mg, at least 1200 U/mg, at least 1400 U/mg, at least 1600 U/mg, at least 1800 U/mg, at least 2000 U/mg, at least 2200 U/mg, at least 2300 U/mg, at least 2400 U/mg and at least 2500 U/mg, wherein the specific activity is determined by incubating the phytase at 67° C. in a solution containing 10 mM phytase, 1 mM $CaCl_2$ in 200 mM sodium acetate buffer at pH 5.5 as detailed in Example 3 of the present disclosure.

In some embodiments, variant phytases according to this disclosure will have a specific activity of at least 800 U/mg, at least 1000 U/mg, at least 1200 U/mg, at least 1400 U/mg, at least 1600 U/mg, at least 1800 U/mg, at least 2000 U/mg, at least 2200 U/mg, at least 2300 U/mg, at least 2400 U/mg, at least 2500 U/mg and at least 2600 U/mg, wherein the specific activity is determined by incubating the phytase at 80° C. in a solution containing 10 mM phytate, 1 mM $CaCl_2$ in 200 mM sodium acetate buffer at pH 5.5 as detailed in example 3 of the present disclosure.

In some embodiments, variant phytases according to this disclosure will be thermostable at 80° C., i.e. retain 50% of activity after exposure to 80° C. for 10 minutes at pH 5.5 and at the same time have a specific activity of at least 2500 U/mg at 80° C. and at least 2300 U/mg at 67° C., wherein the specific activity is determined by incubating the phytase at the specified temperature in a solution containing 10 mM phytate, 1 mM $CaCl_2$ in 200 mM sodium acetate buffer at pH 5.5 as detailed in example 3 of the present disclosure.

In some embodiments, variants encompassed by this disclosure may be used in a method of producing a phosphate compound comprising treating a phytate with a variant phytase encompassed by this disclosure (e.g., variant of SEQ ID NO: 2). The phytate may be myo-inositol di-, tri-, tetra, and/or pentaphosphates. Other suitable organic phosphates include inositol-tetraphosphates and inositol-oligophosphates.

In some embodiments, variants encompassed by this disclosure will retain essentially the same level of specific activity as BP-WT but have an increase in stability at higher temperatures, higher pH, and/or lower pH as compared to BP-WT.

In some embodiments, variants encompassed by this disclosure will retain essentially the same level of specific activity as BP-WT but have an improved thermal activity.

In some embodiments, this disclosure provides a method of producing an enzyme having phytase activity as described herein, comprising: (a) providing a host cell transformed with an expression vector comprising a polynucleotide encoding a phytase variant as described herein, (b) cultivating the transformed host cell under conditions suitable for the host cell to produce the phytase variant; and (c) recovering the phytase variant.

In some embodiments, the expression vector will comprise a polynucleotide which encodes a phytase comprising an amino acid sequence having a substitution in amino acid residues corresponding to positions shown in FIG. 2.

In some embodiments of this disclosure, the host strain is genetically engineered to express heterologous phytases or variants having phytase activity according to this disclosure.

Host cells useful for the production of a phytase encompassed by this disclosure include bacterial cells, fungal cells and plant cells. Host cells include both the cells and progeny of the cells and protoplasts created from the cells which may be used to produce a variant phytase according to this disclosure.

Useful vectors including DNA constructs comprising a polynucleotide encoding a phytase of this disclosure and transformation methods of host cells are well known in the art and standard techniques and methodology may be used.

According to this disclosure, a DNA construct comprising nucleic acid encoding a variant phytase encompassed by this disclosure is constructed to transfer and/or express the variant in a host cell. In one embodiment, the DNA construct is transferred to a host cell by an expression vector which comprises regulatory sequences (e.g. promoters, ribosomal binding sites, transcriptional start and stop sequences, translational start and stop sequences, enhancers, IS activator sequences, cell specific expression sequences, signal sequences, and/or terminators) operably linked to the variant phytase coding sequence.

An expression vector comprising a DNA construct with a polynucleotide encoding variant phytase can be any vector which is capable of replicating autonomously in a given fungal host organism or of integrating into the DNA of the host. In some embodiments, the expression vector is a plasmid or a bacteriophage. In some embodiments, the expression vector is preassembled and contains sequences required for high-level transcription and a selectable marker. In some embodiments, the coding region for variant phytase gene or part thereof is inserted into this general-purpose expression vector such that it is under the transcriptional control of the expression construct promoter and terminator sequences. In some embodiments, genes or part thereof are inserted downstream of the strong cbh1 promoter.

Briefly with respect to production of a phytase in fungal host cells reference in made to Sambrook et al., (1989) supra, Ausubel (1987) supra, van den Hondel et al. (1991) in Bennett and Lasure (Eds.) MORE GENE MANIPULATIONS IN FUNGI, Academic Press (1991) pp. 70-76 and 396-428; Nunberg et al., (1984) *Mol. Cell Biol.* 4:2306-2315; Boel et al., (1984) 30 *EMBO J.* 3:1581-1585; Finkelstein in BIOTECHNOLOGY OF FILAMENTOUS FUNGI, Finkelstein et al. Eds. Butterworth-Heinemann, Boston, Mass. (1992), Chap. 6; Kinghorn et al. (1992) APPLIED MOLECULAR GENETICS OF FILAMENTOUS FUNGI, Blackie Academic and Professional, Chapman and Hall, London; Kelley et al., (1985) *EMBO J.* 4:475-479; Penttila et al., (1987) *Gene* 61: 155-164; and U.S. Pat. No. 5,874,276. A list of suitable vectors may be found in the Fungal Genetics Stock Center Catalogue of Strains (FGSC). Suitable vectors include those obtained from for example Invitrogen Life Technologies and Promega. Specific vectors suitable for use in fungal host cells include vectors such as pFB6, pBR322, pUC 18, pUC100, pDON™201, pDONR™221, pENTR™, pGEM®3Z and pGEM®4Z.

In some embodiments, the vector can be any vector which, when introduced into a fungal host cell, is integrated into the host cell genome and is replicated. Some non-limiting examples of such vectors is provided in the Fungal Genetics Stock Center Catalogue of Strains (FGSC), Additional examples of suitable expression and/or integration vectors are provided in Sambrook et al., (1989) supra, Ausubel (1987) supra, van den Hondel et al. (1991) in Bennett and Lasure (Eds.) MORE GENE MANIPULATIONS IN FUNGI, Academic Press. 396-428 and U.S. Pat. No. 5,874,276. Particularly useful vectors include pTREX, pFB6, pBR322, PUCI8, pUCI00 and pENTR/D. Suitable plasmids for use in bacterial cells include pBR322 and pUC19 permitting replication in *E. coli* and pE194 for example permitting replication in *Bacillus*.

In some embodiments, nucleic acids encoding variant phytase encompassed by this disclosure are operably linked to a suitable promoter, which shows transcriptional activity in the host cell. In general, the expression of the variant phytase is accomplished under any suitable promoter known or later discovered in the art. In some embodiments, the variant phytase is expressed under a promoter native to the host. In some embodiments, the phytase variant is expressed under a heterologous promoter that is active in the host cell. For example, if a *Trichoderma* cell is used as the host cell, then advantageously the promoter is active in a *Trichoderma* host cell.

In some embodiments, the promoter is a constitutive or inducible promoter. A "constitutive promoter" is a promoter that is active under most environmental and developmental conditions. An "inducible" or "repressible" promoter is a promoter that is active under environmental or developmental regulation. In some embodiments, promoters are inducible or repressible due to changes in environmental factors including but not limited to, carbon, nitrogen or other nutrient availability, temperature, pH, osmolarity, the presence of heavy metal(s), the concentration of inhibitor(s), stress, or a combination of the foregoing, as is known in the art. In some embodiments, the inducible or repressible promoters are inducible or repressible by metabolic factors, such as the level of certain carbon sources, the level of certain energy sources, the level of certain catabolites, or a combination of the foregoing as is known in the art. In one embodiment, the promoter is one that is native to the host cell. For example, when *T. reesei* is the host, the promoter is a native *T. reesei* promoter such as the cbh1 promoter which is deposited in GenBank under Accession Number D86235.

Suitable non-limiting examples of promoters include cbh1, cbh2, egl1, egl2, egl3, egl4, egl5, xyn1, and xyn2, repressible acid phosphatase gene (phoA) promoter of *P. chrysogenus* (see e.g., Graessle et al., (1997) *Appl. Environ. Microbiol.*, 63:753-756), glucose repressible PCK1 promoter (see e.g., Leuker et al., (1997), *Gene*, 192:235-240), maltoseinducible, glucose-repressible MET3 promoter (see Liu et al., (2006), *Eukary. Cell*, 5:638-649), pKi promoter and cpc1 promoter. Other examples of useful promoters include promoters from *A. awamori* and *A. niger* glucoamylase genes (see e.g., Nunberg et al., (1984) *Mol. Cell Biol.* 15 4:2306-2315 and Boel et al., (1984) *EMBO J.* 3:1581-1585). Also, the promoters of the *T. reesei* xln1 gene may be useful (see e.g., EPA 137280A1).

In some embodiments, the expression vector also includes a transcription termination sequence downstream of the structural gene to provide for efficient termination. In some embodiments, the termination sequence and the promoter sequence are derived from the same source. In other embodiments, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase gene (see e.g., Nunberg et al. (1984) supra, and Boel et al., (1984) supra).

Methods used to ligate the DNA construct comprising a polynucleotide encoding the phytase variant, a promoter, a terminator and other sequences and to insert them into a suitable vector are well known in the art Linking is generally accomplished by ligation at convenient restriction sites. If such sites do not exist, the synthetic oligonucleotide linkers are used in accordance with conventional practice (see, e.g., Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology). Transformation, expression and culture of host cells.

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion.

Transformation methods for *Aspergillus* and *Trichoderma* are described in, for example, Yelton et al. (1984) Proc. Natl. Acad. Sci. USA 81: 1470-1474; Berka et al., (1991) in Applications of Enzyme Biotechnology, Eds. Kelly and Baldwin, Plenum Press (NY); Cao et al., (2000) *Sci.* 9:991-1001; Campbell et al., (1989) *Curro Genet.* 16:53-56; Pentilla et al., (1987) *Gene* 61:155-164); de Groot et al., (1998) *Nat. Biotechnol.* 16:839-842; U.S. Pat. No. 6,022,725; U.S. Pat. No. 6,268,328 and EP 238 023. The expression of heterologous protein in *Trichoderma* is described in U.S. Pat. No. 6,022, 725; U.S. Pat. No. 6,268,328; Harkki et ale (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to WO96100787 and Bajar et al., (1991) Proc. Natl. Acad. Sci. USA 88:8202-28212 for transformation of *Fusarium* strains.

Methods for making DNA constructs useful in transformation of plants and methods for plant transformation are also known. Some of these methods include *Agrobacterium tumefaciens* mediated gene transfer; microprojectile bombardment, PEG mediated transformation of protoplasts, electroporation and the like. Reference is made to, for example, U.S. Pat. No. 5,780,708; U.S. Pat. No. 6,803,499; U.S. Pat. No. 6,777,589; Fromm et al. (1990) *Biotechnol.* 8:833-839; Potrykus et al. (1985) *Mol. Gen. Genet.* 199:169-177; Brisson et al., (1984) Nature 310:511514; Takamatsu et al., (1987) EMBO J 6:307-311; Coruzzi et al., (1984) EMBO J 3:1671-1680; Broglie et al. (1984) Science 224:838-843; Winter J and Sinibaldi R M (1991) Results Probl Cell Differ 17:85-105; Hobbs S or Murry L E (1992) in McGraw Hill Yearbook of Science and Technology, McGraw Hill, New York, N.Y., pp 191-196; and Weissbach and Weissbach (1988) Methods for Plant Molecular Biology, Academic Press, New York, N.Y., pp 421-463. Transformed cells may be cultured using standard techniques under suitable conditions in shake flask cultivation, small scale or large scale fermentations (including continuous, batch and fed batch fermentations) in laboratory or industrial fermentors, with suitable medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63: 1298-1306). Common commercially prepared media (e.g., Yeast Malt Extract (YM) broth, Luria Bertani (LB) broth and Sabouraud Dextrose (SD) broth find use in the present disclosure. Preferred culture conditions for filamentous fungal cells are known in the art and may be found in the scientific literature and/or from the source of the fungi such as the American Type Culture Collection and Fungal Genetics Stock Center.

In some embodiments, genetically stable transformants are constructed with vector systems whereby the nucleic acid encoding a phytase variant is stably integrated into a host strain chromosome. Transformants are then purified by known techniques.

In order to evaluate the expression of phytase variants having phytase activity by a cell line that has been transformed with a heterologous polynucleotide encoding a phytase variant having phytase activity encompassed by this disclosure, assays can be carried out at the protein level, the RNA level or by use of functional bioassays particular to phytase activity and/or production. In general assays employed include, Northern blotting, dot blotting (DNA or RNA analysis), RT-PCR (reverse transcriptase polymerase chain reaction), or in situ hybridization, using an appropriately labelled probe (based on the nucleic acid coding sequence) and conventional Southern blotting and autoradiography.

In addition, the production and/or expression of a phytase variant having phytase activity may be measured in a sample directly, for example, by assays directly measuring phytase activity (FTU) by the release of inorganic phosphate. The inorganic phosphate forms a yellow complex with acidic vanadate-molybdate reagent and the yellow complex was measured at a wavelength of 415 nm in a spectrophotometer and the released inorganic phosphate was quantified with a phosphate standard curve. One unit of phytase (FTU) is the amount of enzyme that releases 1 micromole of inorganic phosphate (Pi) from phytate per minute.

In addition, gene expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a phytase. The details of such methods are known to those of skill in the art and many reagents for practicing such methods are commercially available.

Assays for phytase activity are well known in the art and one example is the classic assay for liberation of inorganic phosphate developed by Fiske and SubbaRow, *Journal of Biological Chemistry* 66:375-392 (1925). A variation of this method is found in Mitchell et al., *Microbiol.* 143:245-252 (1997). An alternative method is described in FOOD CHEMICALS CODEX, 4th Edition, Committee on Food Chemicals Codex, Institute of Medicine, National Academy Press, Washington, D.C., 1996 at pages 809-810. Each of these references is incorporated herein. In a number of these assays colorimetry is then performed using a spectrophotometer and compared to controls of known concentration of inorganic phosphate (Pi) and/or controls produced by reactions with enzymes having known phytase activity. A Unit of activity is determined as the amount of enzyme sample required to liberate 1 µmol Pi per minute from phytate under defined reaction conditions. Reference is also made to U.S. Pat. No. 6,221,644 and U.S. Pat. No. 6,139,902.

In some embodiments of this disclosure, the phytase variants having phytase activity expressed by a *Trichoderma* or *Aspergillus* host will be greater than 1 gram protein per liter (g/l), greater than 2 g/l, greater than 5 g/l, greater than 10 g/l, greater than 20 g/l, greater than 25 g/l, greater than 30 g/l, greater than 50 g/1 and also greater than 100 g/l of culture media.

The polypeptides produced upon expression of the nucleic acid sequences of this disclosure can be recovered or isolated from the fermentation of cell cultures and substantially purified in a variety of ways according to well established techniques in the art. One of skill in the art is capable of selecting the most appropriate isolation and purification techniques. The phytase of this disclosure can be recovered from culture medium or from host cell lysates. If membrane-bound, it can be released from the membrane using a suitable detergent solution (e.g. Triton-X 100) or by enzymatic cleavage. Cells employed in expression of phytase can be disrupted by various physical or chemical means, such as freeze-thaw cycling, sonication, mechanical disruption, or cell lysing agents. It may be desired to purify the phytase from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants; and metal chelating columns to bind epitope-tagged forms of the phytase. Various methods of protein purification may be employed and such methods are known in the art and described for example in Deutscher, METHODS IN ENZYMOLOGY, 182 (1990); Scopes, PROTEIN PURIFICATION: PRINCIPLES AND PRACTICE, Springer-Verlag, New York (1982). The purification step(s) selected will depend, for example, on the nature of the production process used and the particular form of phytase produced.

In general, a phytase or phytase variant (including the phytase according to SEQ ID NO: 1) produced in cell culture is secreted into the medium and may be purified or isolated, e.g., by removing unwanted components from the cell culture medium. In some cases, the phytase variant can be produced in a cellular form necessitating recovery from a cell lysate. In such cases the enzyme is purified from the cells in which it was produced using techniques routinely employed by those of skill in the art. Examples include, but are not limited to, affinity chromatography (see e.g., Tilbeurgh et al., (1984) *FEBS Lett.* 16:215); ion-exchange chromatographic methods (see e.g. Goyal et al., (1991) *Biores. Technol.* 36:37; Fliess et al., (1983) *Eur. J Appl. Microbiol. Biotechnol.* 17:314; Bhikhabhai et al. (1984) *J Appl. Biochem.* 6:336; and Ellouz et al., (1987) *Chromatography* 396:307), including ion-exchange using materials with high resolution power (see e.g., Medve et al., (1998) *J Chromatography A* 808: 153); hydrophobic interaction chromatography (see e.g., Tomaz and Queiroz, (1999) *J Chromatography A* 865: 123); two-phase partitioning (see e.g., Brumbauer, et al., (1999) *Bioseparation* 7:287); ethanol precipitation; reverse phase HPLC; chromatography on silica or on a cation-exchange resin such as DEAE; chromatofocusing; SDS-PAGE; ammonium sulphate precipitation; and/or gel filtration using, e.g., Sephadex G-75.

In some embodiments of the present disclosure, fungal cells expressing a heterologous phytase variants are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present disclosure. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

In an embodiment of this disclosure, an enzyme composition is provided comprising at least one phytase in accordance with this disclosure. Compositions according to this disclosure may be prepared in accordance with methods known in the art and may be in the form of a liquid or a dry composition.

Liquid compositions need not contain anything more than the phytase enzyme, which typically may be in either a substantially purified or at least partially purified form, although a substantially purified form often will be advantageous. A stabilizer such as glycerol, sorbitol or mono propylene glycol often may be added. The liquid composition may also comprise one or more other additives, such as salts, sugars, preservatives, pH-adjusting agents (i.e., buffering agents), proteins, or phytate (a phytase substrate). Typical liquid compositions are aqueous or oil-based slurries.

Dry compositions may be spray-dried compositions, in which case the composition need not contain anything more than the enzyme in a dry form. Usually, however, dry compositions are so-called granulates which may readily be mixed with for example food or feed components, or more preferably, form a component of a pre-mix. The particle size of the enzyme granulates preferably is compatible with that of the other components of the mixture.

In some embodiments, an enzyme composition including a variant phytase encompassed by this disclosure will be optionally used in combination with anyone or combination of the following enzymes—glucoamylases, alpha amylases, proteases, pullulanases, isoamylases, cellulases, hemicellulases, xylanases, cyclodextrin glycotransferases, lipases, phytases, laccases, oxidases, esterases, cutinases, pectinases, glucose oxidases, beta glucosidases, phosphatases, beta-amylase, hydrolases, transferases other phytases and combinations thereof.

In some embodiments, the phytase composition is a food or animal feed composition. A food or animal feed composition may comprise a phytase at a concentration of 10 to 15,000 U/kg feed or food (e.g. 100 to 5,000 U/kg, 200-2,000 U/kg and also 500-1000 U/kg). The phytase composition may be used as an additive which is active in the digestive tract, of livestock and domestic animals such as poultry, swine, alpaca, bison, camel, cattle, chinchilla, deer, donkey, duck, fish, frog, goat, goose, fowl, horse, llama, mink, mule, ostrich, pigeon, reindeer, sheep, turkey, yak, water buffalo cat, chimpanzee, dog, ferret, gerbil, goldfish, guinea pig, hamster, monkey, parakeet, reptiles and rodents. and aquatic farm animals including fish and shellfish such as shrimp. As compared to the wild type phytase of SEQ. ID NO: 1, the phytase variants of this disclosure can provide improved resistance to the proteases found in such animals or may otherwise provide prolonged activity in the digestive tracts of such animals. The present disclosure contemplates a method for the production of a food or animal feed, characterized in that phytase according to this disclosure is mixed with said food or animal feed for any such animal. The liquid compositions can be added to a food or feed after an optional pelleting thereof. In some embodiments, the animal feed will comprise one or more of the following components: a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins; f) supplements, such as enzymes, betaine, flavors, essential oils, antibiotic growth promoters, coccidiostats, probiotics, and prebiotics.

Also provided is a method for the reduction of levels of phosphorus in animal manure, characterized in that an animal is fed with an animal feed comprising a phytase variant according to this disclosure in an amount effective in converting phytate contained in said animal feed.

Further the phytase compositions encompassed by this disclosure may be used in methods of starch hydrolysis. The phytase composition may be added during a starch liquefaction step, a saccharification step and/or during a fermentation step. Alpha-amylases are used to break down starch 1-4 linkages during industrial starch hydrolysis processes using reduced plant material such as milled grains as a feedstock (e.g. in fermentation processes, brewing, and baking). Amylases are required to break down starch and obtaining adequate activity of these enzymes is sometimes problematic. It has been known for some time that phytate has an inhibitory effect on amylases. Therefore enzyme compositions comprising a phytase according to this disclosure may be used in starch hydrolysis process to reduce the inhibitory effect of phytate on alpha amylase (EP 0 813607B1).

Phytases, phytate and lower phosphate phytate derivatives find many other uses in personal care products, medical products and food and nutritional products, as well as various industrial applications, particularly in the cleaning, textile, lithographic and chemical arts. Advantageously, for example, phytase variants according to embodiments of the present disclosure can be used in alcohol fermentation, e.g. for the production of biofuel.

Use of Phytases

As stated above, the present invention also relates to the production of phytases as described herein.

In particular, the present invention also relates to the use of the amino acid sequences as disclosed herein in the production of organic and inorganic phosphate compounds.

Thus, the present invention further relates to the use of the nucleotide sequences encoding phytases in generating expression vectors or systems for the expression of the phytases.

In addition, the present invention relates to the use of such expression vectors or systems in the generation of host cells which express phytases.

The invention further relates to the use of modified host cells in the generation of precursors of organic and inorganic phosphate compounds or in the generation of specific organic phosphate compounds.

Suitable organic and inorganic phosphate compounds include myo-inositol pentakis-, tetrakis-, tris-, bis- and monophosphates.

Suitably, the invention therefore provides a method of producing an organic phosphate compound comprising treating a phytate with a phytase according to the present invention. Suitably, the organic phosphate is phytate or all possible stereoisomers of myo-inositol di-, tri-, tetra, and pentaphosphates. Other suitable organic phosphates include inositol-tetraphosphates and inositol-oligophosphates. In a preferred embodiment, the method is an in vivo biotechnological process.

Such methods for producing an organic phosphate compound may suitably comprise the steps of:
a) providing a host cell that comprises expressible transgenes comprising the phytase of the invention;
b) culturing the transgenic organism under conditions suitable for expression of the transgene; and
c) recovering the organic phosphate compound from the culture.

The compounds can be used for a number of applications including in assays for the characterisation of phytases. Some inositol phosphates are involved as signal molecules in intracellular regulation and can be used research chemicals.

In another aspect there is provided a method for production of food or animal feed. Animal feed is typically produced in feed mills in which raw materials are first ground to a suitable particle size and then mixed with appropriate additives. The feed may then be produced as a mash or pellets; the later typically involves a method by which the temperature is raised to a target level and then the feed is passed through a die to produce pellets of a particular size. Subsequently liquid additives such as fat and enzyme may be added. The pellets are allowed to cool prior to transportation. Production of animal feed may also involve an additional step that includes extrusion or expansion prior to pelleting—in particular by suitable techniques, that may include at least the use of steam.

Accordingly, the invention further provides the use of an amino acid sequence encoding a phytase or a host cell expressing a phytase to produce a phytase for use in the manufacture of a food or feed product. In one aspect, there is provided a use of an amino acid sequence as described herein in the manufacture of a food or feed product. In another aspect, there is provided a use of a host cell in accordance with the invention in the manufacture of a food or feed product. In another aspect, there is provided a use of an expression vector or system in accordance with the invention in the manufacture of a food or feed product.

The present invention also covers using the enzymes as a component of feed combinations with other components to deliver to animals.

Combination with Other Components

The enzymes of the present invention may be used in combination with other components or carriers. Examples of other components have already been provided herein. These and other additional components are now discussed.

Suitable carriers for feed enzymes include wheat (coarsely ground). In addition there are a number of encapsulation techniques including those based on fat/wax coverage, adding plant gums etc.

Examples of other components include one or more of: thickeners, gelling agents, emulsifiers, binders, crystal modifiers, sweetners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions.

As used herein the term "binder" refers to an ingredient (e.g. a food ingredient) that binds the product together through a physical or chemical reaction.

The term "crystal modifier" as used herein refers to an ingredient (e.g. a food ingredient) that affects the crystallisation of either fat or water.

"Carriers" or "vehicles" mean materials suitable for compound administration and include any such material known in the art such as, for example, any liquid, gel, solvent, liquid diluent, solubiliser, or the like, which is non-toxic and which does not interact with any components of the composition in a deleterious manner.

Examples of nutritionally acceptable carriers include, for example, grain, water, salt solutions, alcohol, silicone, waxes, petroleum jelly, vegetable oils, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g when they are in admixture together or even when they are delivered by different routes) or sequentially (e.g they may be delivered by different routes).

As used herein the term "component suitable for animal or human consumption" means a compound which is or can be added to the composition of the present invention as a supplement which may be of nutritional benefit, a fibre substitute or have a generally beneficial effect to the consumer.

By way of example, the components may be prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

Food or Feed Substance

The compounds may be used as—or in the preparation of—a food or feed substance. Here, the term "food" is used in a broad sense—and covers food and food products for humans as well as food for animals (i.e. a feed). The term "feed" is used with reference to products that are fed to animals in the rearing of livestock. In a preferred aspect, the food or feed is for consumption by monogastric animals such as pig, poultry and fish.

The food or feed may be in the form of a solution or as a solid—depending on the use and/or the mode of application and/or the mode of administration.

Food and Feed Ingredients and Supplements

The compounds may be used as a food or feed ingredient.

As used herein the term "food or feed ingredient" includes a formulation, which is or can be added to foods or foodstuffs and includes formulations which can be used at low levels in a wide variety of products.

The food ingredient may be in the form of a solution or as a solid—depending on the use and/or the mode of application and/or the mode of administration.

The compounds may be—or may be added to—food supplements.

Foods and Feed Compositions

Feed compositions for monogastric animals typically include compositions comprising plant products which contain phytate. Such compositions include cornmeal, soybean meal, rapeseed meal, cottonseed meal, maize, wheat, barley and sorghum-based feeds.

The phytases described herein may be—or may be added to—foods or feed substances and compositions.

The present invention also provides a method of preparing a food or a feed ingredient or supplement, the method comprising admixing phytases produced by the process of the present invention or the composition according to the present invention with another food ingredient. The method for preparing or a food ingredient is also another aspect of the present invention. Methods for preparing animal feed are set out above. The enzyme can be added also in the form of a solid formulation, or as a feed additive, such as a pre-mix. A solid form is typically added before or during the mixing step; and a liquid form is typically added after the pelleting step.

Forms

The product and/or the compounds of the present invention may be used in any suitable form—whether when alone or when present in a composition. Likewise, phytases produced in accordance with the present invention (i.e. ingredients—such as food ingredients, functional food ingredients or pharmaceutical ingredients) may be used in any suitable form.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the product and/or the composition are used in a tablet form—such as for use as a functional ingredient—the tablets may also contain one or more of: excipients, disintegrants, granulation binders, or lubricating agents.

Examples of nutritionally acceptable carriers for use in preparing the forms include, for example, water, salt solutions, alcohol, silicone, waxes, petroleum jelly and the like.

Preferred excipients for the forms include lactose, starch, a cellulose, milk sugar or high molecular weight polyethylene glycols.

For aqueous suspensions and/or elixirs, the phytase cleavage compounds may be combined with various sweetening or flavouring agents, colouring matter or dyes, with emulsifying and/or suspending agents and with diluents such as water, ethanol, propylene glycol and glycerin, and combinations thereof.

The forms may also include gelatin capsules; fibre capsules, fibre tablets etc.

The following examples are offered for illustrative purposes only, and are not intended to limit the scope of the present disclosure in any way.

METHODS AND EXAMPLES

Nomenclature for Enzymes Used in the Examples

Phytase BP-17 (sometimes referred to as BP 17)—which is the phytase described in at least PCT application WO 2008/097619 and which may be obtained from Danisco A/S. The amino acid sequence is described herein as SEQ ID NO:5.

BP-110 (sometimes referred to as BP 17 var. 110, or sometimes it is referred to as BP17-110 or BP17 110)—which is the phytase according to the present invention and which may be obtained from Danisco A/S. The amino acid sequence is described herein as SEQ ID NO:6.

BP-111 (sometimes referred to as BP 17 var. 111, or sometimes it is referred to as BP17-111 or BP17 111)—which is the phytase according to the present invention and which may be obtained from Danisco A/S. The amino acid sequence is described herein as SEQ ID NO:7.

BP-112 (sometimes referred to as BP 17 var. 112, or sometimes it is referred to as BP17-112 or BP17 112)—which is the phytase according to the present invention and which may be obtained from Danisco A/S. The amino acid sequence is described herein as SEQ ID NO:2.

The amino acid sequences for BP-17 (SEQ ID NO: 5), BP-110 (SEQ ID NO:6), BP-111 (SEQ ID NO:7) and BP-112 (SEQ ID NO:2) are presented in FIG. 5. The amino acid sequence of BP-112 is also shown in FIG. 2. The nucleic acid sequence of BP-112 is shown in FIG. 4 as SEQ ID NO:4.

Phyzyme XP—which is a phytase from Danisco A/S
Natuphos—which is a phytase from BASF.
Ronozyme P—which is a phytase from Novozymes.

Part A

Example 1

Purification of Phytase Enzymes

Purification of phytase enzymes was performed using a 6His-tag N-terminally fused to the phytase enzymes. *B. subtilis*, transformed with a plasmid coding for the 6His-tagged phytase enzyme, was cultivated in shake flasks at 37° C. and 160 rpm using standard LB medium with addition of 20 mg/l Neomycin. At this stage, the culture medium accumulated significant amount of phytase activity. About 2 l of the culture broth were adjusted to pH 8.0, filtered and applied to a column packed with 10 ml of Ni-NTA sepharose resin (Qiagen). The column was washed with 50 mM Tris-HCl buffer, 300 mM NaCl, pH 8.0 until OD280 dropped below 0.05. Subsequently the bound phytase was eluted with the same buffer containing 250 mM imidazole hydrochloride. The elutate was dialysed against 50 mM sodium acetate buffer pH 5.0 and stored at 4° C. The enzyme solution was then applied to a Resource S column equilibrated with 20 mM sodium acetate buffer pH 5.0 and the elution was performed using a salt gradient from 0-1 M NaCl over 10 column volumes. Optionally the eluate was dialysed against 20 mM sodium acetate buffer pH 5.0 before storing at 4° C.

Example 2

Phytase Activity Assay

Phytase assays were carried out in microtiter plates. The reaction had a total volume of 100 microliter containing buffer, as described below, 10 mM phytate, 1 mM calcium chloride and 0.05% (w/v) Pluronic F68. The reaction was allowed to proceed for 30 minutes at a given temperature, e.g. between 37° C. and 90° C.

Phosphate liberation from phytate as a measure of the phytase activity was assayed by incubating aliquots of the samples (typically 5 μl) in a total volume of 50 μl of phosphate detection assay for 1 h at 37° C. The assay contained the following compounds at the given final concentrations: 1 M Tris/HCl, pH 7.0, 0.01% (v/v) Triton X-100, 0.025 mM ADHP (MoBiTec, Göttingen, Germany), 0.2 U/ml maltose-phosphorylase, 0.25 mM maltose, 1.25 U/ml glucose oxidase, 0.25 U/ml horseradish peroxidase, 1 mM EDTA, 0.35 mg/ml BSA. The reaction was stopped by the addition of 30 μl of 2700 U/ml catalase in H2O. Subsequently the fluorescence at 595 nm was measured, using 535 nm as excitation wavelenght. The amount of phosphate was determined using a calibration curve with phosphate solutions of known concentrations. One enzymatic unit is defined as the liberation of one micromole phosphate per minute.

For assaying phytase activity at different pH values the following buffers were used: 200 mM glycine/HCl from pH 2.0 to pH 3.5 and 100 mM sodium acetate/acetic acid between pH 4.0 and pH 5.5.

Example 3

Specific Activity

The specific activity of BP-WT and variant phytase enzymes was estimated using the purified enzymes according to example 1.

Phytase activity was determined in microtiter plates using a coupled enzymatic assay: Enzyme preparations were diluted in dilution buffer (50 mM sodium acetate, 0.05% Pluronic F-68, 1 mg/ml BSA). An aliquot of the enzyme solution, typically 5 µl to 10 µl was incubated in the phytate assay with a total volume of 80 The assay contains the following buffers, substrates and salts at the given final concentrations: 200 mM sodium acetate, pH 5.5, 10 mM phytate, 1 mM CaCl2, 0.05% (w/v) Pluronic F-68). The assays were incubated for 30 min at 37° C. in the case of the BP-WT phytase and for 30 min at 67° C. or 80° C. in the case of the variant phytase enzymes.

Phosphate liberation from phytate as a measure of the phytase activity was assayed by incubating aliquots of the respective samples (typically 5 µl) in a total volume of 50 µl of phosphate detection assay for 1 h at 37° C. The assay contained the following compounds at the given final concentrations: 1 M Tris/HCl, pH 7.0, 0.01% (v/v) Triton X-100, 0.025 mM ADHP (MoBiTec, Göttingen, Germany), 0.2 U/ml maltosephosphorylase, 0.25 mM maltose, 1.25 U/ml glucose oxidase, 0.25 U/ml horseradish peroxidase, 1 mM EDTA, 0.35 mg/ml BSA. The reaction was stopped by the addition of 30 µl of 2700 U/ml catalase in H2O. Subsequently the fluorescence at 595 nm was measured, using 535 nm as excitation wavelength. The amount of phosphate was determined using a calibration curve with phosphate solutions of known concentrations. One enzymatic unit is defined as the liberation of one micromole phosphate per minute.

Phytase concentration was calculated from the absorbance of the preparations at 280 nm and the respective extinction coefficient for each of each phytase variant. The extinction coefficients were calculated on the basis of the amino acid composition of the proteins according to a method provided by Gill and von Hippel, Analytical Biochemistry 182:319-326 (1989).

TABLE 1

Specific activity of phytase variants according to BP-WT, Seq ID No. 1. The specific activity of the variant phytase enzymes was determined at 67° C. and 80° C. as described above. The BP-WT enzyme has a specific activity of 1021 U/mg at 37° C. under the conditions described above.

| Variant | Specific activity at 67° C./[U/mg] | Specific activity at 80° C./[U/mg] |
|---|---|---|
| N37Y/S75P/A89T/D92A/T134I/H160R/F164E/T171V/T176K/A178P/S188P/G192A/K198R/K207E/A209S/S248L/Q256Y/A261E/N270K/A374P [BP-112] | 2381 | 2592 |
| N37Y/G77S/A89T/D92A/T134I/H160R/F164E/T171V/T176K/A178P/S188P/G192A/K198R/K207E/A209S/S248L/Q256Y/A261E/N270K/A374P [BP-110] | 2192 | 2315 |
| N37Y/S75P/Q76R/A89T/D92A/T134I/H160R/F164E/T171I/T176K/A178P/S188P/G192A/K207E/A209S/A235V/S248L/Q256Y/A261E/N270K/A374P [BP-111] | 2065 | 2052 |
| N37Y/A89T/D92A/T134I/F164E/T171V/T176K/A178P/G192A/K207E/A209S/A235V/S248L/Q256P/A261E/N270K/A374P | 1725 | 1652 |
| S75P/Q76R/A89T/D92A/T134I/H160R/F164E/T171I/T176K/A178P/S188P/G192A/K207E/A209S/S248L/Q256Y/A261E/N270K/A374P | 1680 | 1481 |
| N37Y/Q76R/A89T/D92A/T134I/H160R/F164E/T171I/T176K/A178P/S188P/G192A/K207E/A209S/S248L/Q256Y/A261E/N270K/A374P | 2441 | 1948 |
| N37Y/Q76R/A89T/D92A/T134I/F164S/T171V/T176K/A178P/S188P/G192A/K207E/A209S/A235V/S248L/Q256A/A261E/N270K/A374P | 1613 | 1412 |
| S75P/A89T/D92A/T134I/F164E/T171V/T176K/A178P/S188P/G192A/K207E/A209S/A235V/S248L/Q256Y/A261E/N270K/A374P | 2171 | 1820 |
| S75P/Q76R/A89T/D92A/T134I/H160R/F164E/T171V/T176K/A178P/S188P/G192A/K207E/A209S/A235V/S248L/Q256Y/A261E/N270K/P367L/A374P | 2421 | 2038 |
| N37Y/A89T/D92A/T134I/F164E/T171I/T176K/A178P/G192A/K207E/A209S/A235V/S248L/Q256Y/A261E/N270K/A374P | 2314 | 1752 |
| N37Y/Q76R/A89T/D92A/T134I/F164E/T171V/T176K/A178P/G192A/K207E/A209S/S248L/Q256Y/A261E/N270K/A374P | 2251 | 1783 |
| N37Y/Q76R/A89T/D92A/T134I/F164E/T171V/T176K/A178P/G192A/K207E/A209S/S248L/Q256A/A261E/N270K/A374P | 1597 | 1289 |
| N37Y/S75P/Q76R/A89T/D92A/T134I/F164E/T171V/T176K/A178P/K207E/A209S/A235V/S248L/Q256A/A261E/N270K/A374P | 1651 | 1104 |
| N37Y/S75P/A89T/D92A/T134I/H160R/F164E/T171V/T176K/A178P/K207E/A209S/A235V/S248L/Q256Y/A261E/N270K/A374P | 2378 | 1750 |
| N37Y/A89T/D92A/T134I/H160R/F164S/T171I/T176K/A178P/S188P/G192A/K207E/A209S/A235V/S248L/Q256E/A261E/N270K/A374P | 2010 | 1392 |
| A89T/D92A/T134I/H160R/F164E/T171V/T176K/A178P/G192A/K207E/A209S/A235V/S248L/Q256Y/A261E/N270K/A374P | 2161 | 1468 |

TABLE 1-continued

Specific activity of phytase variants according to BP-WT, Seq ID No. 1. The specific activity of the variant phytase enzymes was determined at 67° C. and 80° C. as described above. The BP-WT enzyme has a specific activity of 1021 U/mg at 37° C. under the conditions described above.

| Variant | Specific activity at 67° C./[U/mg] | Specific activity at 80° C./[U/mg] |
|---|---|---|
| N37Y/S75P/A89T/D92A/T134I/H160R/F164S/T171V/T176K/A178P/S188P/K207E/A209S/S248L/Q256H/A261E/N270K/A374P | 2421 | 962 |
| N37Y/S75P/A89T/D92A/T134I/F164S/T171V/T176K/A178P/S188P/G192A/K207E/A209S/S248L/Q256A/A261E/N270K/A374P | 1866 | 998 |
| S75P/Q76R/A89T/D92A/T134I/H160R/F164E/T171V/T176K/A178P/G192A/K207E/A209S/S248L/Q256A/A261E/N270K/A374P | 1755 | 843 |
| N37Y/Q76R/A89T/D92A/T134I/H160R/F164S/T171V/T176K/A178P/G192A/K207E/A209S/A235V/S248L/Q256Y/A261E/N270K/A374P | 2476 | 1654 |

Example 4

Generation and Characterization of Phytase Variants

Phytase variants were generated using different methods for the mutagenesis of the DNA encoding the phytase proteins like cassette or PCR mutagenesis or other mutagenesis methods well known in the art. Those methods comprise the ones listed above such as the methods disclosed in Morinaga et al., *Biotechnology* 2:646-649 (1984); in Nelson and Long, *Analytical Biochemistry* 180:147-151(1989); or the Error Threshold Mutagenesis protocol described in WO 92/18645. For mutagenic PCR another suitable method is disclosed by Cadwell and Joyce, *PCR Methods Appl.* 3:136-140(1994).

Phytase variants were heterologously expressed in one or more of the following expression hosts: *Saccharomyces cerevisiae, Bacillus subtilis, Escherichia coli*.

Example 5

Thermal Stability

The thermal stability of phytase variants was characterized by their inactivation temperature. The inactivation temperature was determined by the residual activity of the phytase enzymes after incubation for 10 min at different temperatures, pH 5.5 and subsequent incubation at 37° C. for 60 min. Residual activities were determined measuring phytase activities for 60 min at pH 3.5 and 37° C. The inactivation temperature is defined as the temperature at which the residual activity is 50% compared to the residual activity after incubation for the same duration under the same conditions at room temperature. Where appropriate extrapolations and interpolations from the activity data were made in order to determine the temperature corresponding to 50% residual activity. Thermal stability differences (TD) in [° C.] were calculated by subtracting the inactivation temperatures of two enzymes from each other.

TABLE 2

Thermal stability of phytase variants according to BT-WT, Seq ID No. 1. Improvements in thermal stability are presented as thermal stability differences TD between variant and wild-type (BP-WT) phytase enzyme, i.e. TD = (inactivation temperature of the variant phytase)—(inactivation temperature of BP-WT).

| Variant | TD/[° C.] |
|---|---|
| N37Y/S75P/A89T/D92A/T134I/H160R/F164E/T171V/T176K/A178P/S188P/G192A/K198R/K207E/A209S/S248L/Q256Y/A261E/N270K/A374P [BP-112] | 26.5 |
| N37Y/G77S/A89T/D92A/T134I/H160R/F164E/T171V/T176K/A178P/S188P/G192A/K198R/K207E/A209S/S248L/Q256Y/A261E/N270K/A374P [BP-110] | 25.9 |
| N37Y/S75P/Q76R/A89T/D92A/T134I/H160R/F164E/T171I/T176K/A178P/S188P/G192A/K207E/A209S/A235V/S248L/Q256Y/A261E/N270K/A374P [BP-111] | 26.8 |
| N37Y/A89T/D92A/T134I/F164E/T171V/T176K/A178P/G192A/K207E/A209S/A235V/S248L/Q256P/A261E/N270K/A374P | 23.7 |
| S75P/Q76R/A89T/D92A/T134I/H160R/F164E/T171I/T176K/A178P/S188P/G192A/K207E/A209S/S248L/Q256Y/A261E/N270K/A374P | 24.2 |
| N37Y/Q76R/A89T/D92A/T134I/H160R/F164E/T171I/T176K/A178P/S188P/G192A/K207E/A209S/S248L/Q256Y/A261E/N270K/A374P | 25.0 |
| N37Y/Q76R/A89T/D92A/T134I/F164S/T171V/T176K/A178P/S188P/G192A/K207E/A209S/A235V/S248L/Q256A/A261E/N270K/A374P | 22.6 |
| S75P/A89T/D92A/T134I/F164E/T171V/T176K/A178P/S188P/G192A/K207E/A209S/A235V/S248L/Q256Y/A261E/N270K/A374P | 24.9 |
| S75P/Q76R/A89T/D92A/T134I/H160R/F164E/T171V/T176K/A178P/S188P/G192A/K207E/A209S/A235V/S248L/Q256Y/A261E/N270K/P367L/A374P | 24.1 |

TABLE 2-continued

Thermal stability of phytase variants according to BT-WT, Seq ID No. 1. Improvements in thermal stability are presented as thermal stability differences TD between variant and wild-type (BP-WT) phytase enzyme, i.e. TD = (inactivation temperature of the variant phytase)—(inactivation temperature of BP-WT).

| Variant | TD/[° C.] |
|---|---|
| N37Y/A89T/D92A/T134I/F164E/T171I/T176K/A178P/G192A/K207E/A209S/A235V/S248L/Q256Y/A261E/N270K/A374P | 23.4 |
| N37Y/Q76R/A89T/D92A/T134I/F164E/T171V/T176K/A178P/G192A/K207E/A209S/S248L/Q256Y/A261E/N270K/A374P | 23.5 |
| N37Y/Q76R/A89T/D92A/T134I/F164E/T171V/T176K/A178P/G192A/K207E/A209S/S248L/Q256A/A261E/N270K/A374P | 24.4 |
| N37Y/S75P/Q76R/A89T/D92A/T134I/F164E/T171V/T176K/A178P/K207E/A209S/A235V/S248L/Q256A/A261E/N270K/A374P | 22.4 |
| A89T/D92A/T134I/H160R/F164E/T171V/T176K/A178P/G192A/K207E/A209S/A235V/S248L/Q256Y/A261E/N270K/A374P | 23.5 |
| S75P/Q76R/A89T/D92A/T134I/H160R/F164E/T171V/T176K/A178P/G192A/K207E/A209S/S248L/Q256A/A261E/N270K/A374P | 22.9 |

Example 6

Thermal Activity

The thermal activity of phytase variants was characterized by their temperature-activity profile. As a measure of the temperature-activity profile the value T50 was defined, at which the total enzymatic turnover of the substrate is 50% compared to the total enzymatic turnover of the substrate in a reaction running essentially under the same conditions but at the temperature optimum of the phytase variant. The temperature-activity profiles were determined by incubation of the phytase enzymes at pH 5.5 and various temperatures under conditions further described in Example 2. T50 values were determined by appropriate interpolations and extrapolations from the experimental data. Thermal activity differences (TAD) in [° C.] were calculated by subtracting the T50 values of two enzymes from each other.

TABLE 3

Thermal activity differences (TAD) of phytase variants according to BT-WT, Seq ID No: 1. Improvements in thermal activity are given as T50 differences between variant and wild-type (BP-WT) phytase enzyme, i.e. TAD = T50(variant phytase) − T50(BP-WT).

| Variant | TAD/[° C.] |
|---|---|
| N37Y/S75P/A89T/D92A/T134I/H160R/F164E/T171V/T176K/A178P/S188P/G192A/K198R/K207E/A209S/S248L/Q256Y/A261E/N270K/A374P [BP-112] | 20.2 |
| N37Y/G77S/A89T/D92A/T134I/H160R/F164E/T171V/T176K/A178P/S188P/G192A/K198R/K207E/A209S/S248L/Q256Y/A261E/N270K/A374P [BP-110] | 20.0 |
| N37Y/S75P/Q76R/A89T/D92A/T134I/H160R/F164E/T171I/T176K/A178P/S188P/G192A/K207E/A209S/A235V/S248L/Q256Y/A261E/N270K/A374P [BP-111] | 20.1 |
| N37Y/A89T/D92A/T134I/F164E/T171V/T176K/A178P/G192A/K207E/A209S/A235V/S248L/Q256P/A261E/N270K/A374P | 19.5 |
| S75P/Q76R/A89T/D92A/T134I/H160R/F164E/T171I/T176K/A178P/S188P/G192A/K207E/A209S/S248L/Q256Y/A261E/N270K/A374P | 19.3 |
| N37Y/Q76R/A89T/D92A/T134I/H160R/F164E/T171I/T176K/A178P/S188P/G192A/K207E/A209S/S248L/Q256Y/A261E/N270K/A374P | 19.3 |
| N37Y/Q76R/A89T/D92A/T134I/F164S/T171V/T176K/A178P/S188P/G192A/K207E/A209S/A235V/S248L/Q256A/A261E/N270K/A374P | 18.9 |
| S75P/A89T/D92A/T134I/F164E/T171V/T176K/A178P/S188P/G192A/K207E/A209S/A235V/S248L/Q256Y/A261E/N270K/A374P | 19.0 |
| S75P/Q76R/A89T/D92A/T134I/H160R/F164E/T171V/T176K/A178P/S188P/G192A/K207E/A209S/A235V/S248L/Q256Y/A261E/N270K/P367L/A374P | 18.9 |
| N37Y/A89T/D92A/T134I/F164E/T171I/T176K/A178P/G192A/K207E/A209S/A235V/S248L/Q256Y/A261E/N270K/A374P | 18.8 |
| N37Y/Q76R/A89T/D92A/T134I/F164E/T171V/T176K/A178P/G192A/K207E/A209S/S248L/Q256Y/A261E/N270K/A374P | 18.7 |
| N37Y/Q76R/A89T/D92A/T134I/F164E/T171V/T176K/A178P/G192A/K207E/A209S/S248L/Q256A/A261E/N270K/A374P | 18.9 |
| N37Y/S75P/Q76R/A89T/D92A/T134I/F164E/T171V/T176K/A178P/K207E/A209S/A235V/S248L/Q256A/A261E/N270K/A374P | 18.4 |
| N37Y/S75P/A89T/D92A/T134I/H160R/F164E/T171V/T176K/A178P/K207E/A209S/A235V/S248L/Q256Y/A261E/N270K/A374P | 17.9 |
| N37Y/A89T/D92A/T134I/H160R/F164S/T171I/T176K/A178P/S188P/G192A/K207E/A209S/A235V/S248L/Q256E/A261E/N270K/A374P | 17.9 |
| A89T/D92A/T134I/H160R/F164E/T171V/T176K/A178P/G192A/K207E/A209S/A235V/S248L/Q256Y/A261E/N270K/A374P | 17.8 |
| N37Y/S75P/A89T/D92A/T134I/H160R/F164S/T171V/T176K/A178P/S188P/K207E/A209S/S248L/Q256H/A261E/N270K/A374P | 17.8 |
| N37Y/S75P/A89T/D92A/T134I/F164S/T171V/T176K/A178P/S188P/G192A/K207E/A209S/S248L/Q256A/A261E/N270K/A374P | 17.4 |

TABLE 3-continued

Thermal activity differences (TAD) of phytase variants according to BT-WT, Seq ID No: 1. Improvements in thermal activity are given as T50 differences between variant and wild-type (BP-WT) phytase enzyme, i.e. TAD = T50(variant phytase) − T50(BP-WT).

| Variant | TAD/ [° C.] |
|---|---|
| S75P/Q76R/A89T/D92A/T134I/H160R/F164E/T171V/T176K/A178P/G192A/K207E/ A209S/S248L/Q256A/A261E/N270K/A374P | 17.5 |
| N37Y/Q76R/A89T/D92A/T134I/H160R/F164S/T171V/T176K/A178P/G192A/ K207E/A209S/A235V/S248L/Q256Y/A261E/N270K/A374P | 17.6 |

Example 7

Properties Overview of Phytase Variants i) Table 4 summarizes the properties specific activity, thermal stability and thermal activity of phytase variants that were before presented in examples 3, 5 and 6.

TABLE 4

Specific activity, thermal stability and thermal activity of different phytase variants according to BT-WT, Seq ID No: 1. Values for specific activities, thermal stability (TD), and thermal activity (TAD) were derived as described in example 3, example 5 and example 6, respectively.

| Variant | TD/ [° C.] | TAD/ [° C.] | Specific activity at 67° C./[U/mg] | Specific activity at 80° C./[U/mg] |
|---|---|---|---|---|
| N37Y/S75P/A89T/D92A/T134I/H160R/F164E/ T171V/T176K/A178P/S188P/G192A/ K198R/K207E/A209S/S248L/Q256Y/A261E/ N270K/A374P [BP-112] | 26.5 | 20.2 | 2381 | 2592 |
| N37Y/G77S/A89T/D92A/T134I/H160R/F164E/ T171V/T176K/A178P/S188P/G192A/ K198R/K207E/A209S/S248L/Q256Y/A261E/ N270K/A374P [BP-110] | 25.9 | 20.0 | 2192 | 2315 |
| N37Y/S75P/Q76R/A89T/D92A/T134I/H160R/ F164E/T171I/T176K/A178P/S188P/G192A/ K207E/A209S/A235V/S248L/Q256Y/ A261E/N270K/A374P [BP-110] | 26.8 | 20.1 | 2065 | 2052 |
| N37Y/A89T/D92A/T134I/F164E/T171V/T176K/ A178P/G192A/K207E/A209S/A235V/ S248L/Q256P/A261E/N270K/A374P | 23.7 | 19.5 | 1725 | 1652 |
| S75P/Q76R/A89T/D92A/T134I/H160R/F164E/ T171I/T176K/A178P/S188P/G192A/K207E/ A209S/S248L/Q256Y/A261E/N270K/ A374P | 24.2 | 19.3 | 1680 | 1481 |
| N37Y/Q76R/A89T/D92A/T134I/H160R/F164E/ T171I/T176K/A178P/S188P/G192A/K207E/ A209S/S248L/Q256Y/A261E/N270K/ A374P | 25.0 | 19.3 | 2441 | 1948 |
| N37Y/Q76R/A89T/D92A/T134I/F164S/T171V/ T176K/A178P/S188P/G192A/K207E/ A209S/A235V/S248L/Q256A/A261E/N270K/ A374P | 22.6 | 18.9 | 1613 | 1412 |
| S75P/A89T/D92A/T134I/F164E/T171V/T176K/ A178P/S188P/G192A/K207E/A209S/ A235V/S248L/Q256Y/A261E/N270K/A374P | 24.9 | 19.0 | 2171 | 1820 |
| S75P/Q76R/A89T/D92A/T134I/H160R/F164E/ T171V/T176K/A178P/S188P/G192A/K207E/ A209S/A235V/S248L/Q256Y/A261E/ N270K/P367L/A374P | 24.1 | 18.9 | 2421 | 2038 |
| N37Y/A89T/D92A/T134I/F164E/T171I/T176K/ A178P/G192A/K207E/A209S/A235V/ S248L/Q256Y/A261E/N270K/A374P | 23.4 | 18.8 | 2314 | 1752 |
| N37Y/Q76R/A89T/D92A/T134I/F164E/T171V/ T176K/A178P/G192A/K207E/A209S/ S248L/Q256Y/A261E/N270K/A374P | 23.5 | 18.7 | 2251 | 1783 |
| N37Y/Q76R/A89T/D92A/T134I/F164E/T171V/ T176K/A178P/G192A/K207E/A209S/ S248L/Q256A/A261E/N270K/A374P | 24.4 | 18.9 | 1597 | 1289 |

TABLE 4-continued

Specific activity, thermal stability and thermal activity of different phytase variants according to BT-WT, Seq ID No: 1. Values for specific activities, thermal stability (TD), and thermal activity (TAD) were derived as described in example 3, example 5 and example 6, respectively.

| Variant | TD/ [° C.] | TAD/ [° C.] | Specific activity at 67° C./[U/mg] | Specific activity at 80° C./[U/mg] |
|---|---|---|---|---|
| N37Y/S75P/Q76R/A89T/D92A/T134I/F164E/T171V/T176K/A178P/K207E/A209S/A235V/S248L/Q256A/A261E/N270K/A374P | 22.4 | 18.4 | 1651 | 1104 |
| N37Y/S75P/A89T/D92A/T134I/H160R/F164E/T171V/T176K/A178P/K207E/A209S/A235V/S248L/Q256Y/A261E/N270K/A374P | n.d. | 17.9 | 2378 | 1750 |
| N37Y/A89T/D92A/T134I/H160R/F164S/T171I/T176K/A178P/S188P/G192A/K207E/A209S/A235V/S248L/Q256E/A261E/N270K/A374P | n.d. | 17.9 | 2010 | 1392 |
| A89T/D92A/T134I/H160R/F164E/T171V/T176K/A178P/G192A/K207E/A209S/A235V/S248L/Q256Y/A261E/N270K/A374P | 23.5 | 17.8 | 2161 | 1468 |
| N37Y/S75P/A89T/D92A/T134I/H160R/F164S/T171V/T176K/A178P/S188P/K207E/A209S/S248L/Q256H/A261E/N270K/A374P | n.d. | 17.8 | 2421 | 962 |
| N37Y/S75P/A89T/D92A/T134I/F164S/T171V/T176K/A178P/S188P/G192A/K207E/A209S/S248L/Q256A/A261E/N270K/A374P | n.d. | 17.4 | 1866 | 998 |
| S75P/Q76R/A89T/D92A/T134I/H160R/F164E/T171V/T176K/A178P/G192A/K207E/A209S/S248L/Q256A/A261E/N270K/A374P | 22.9 | 17.5 | 1755 | 843 |
| N37Y/Q76R/A89T/D92A/T134I/H160R/F164S/T171V/T176K/A178P/G192A/K207E/A209S/A235V/S248L/Q256Y/A261E/N270K/A374P | n.d. | 17.6 | 2476 | 1654 |

Part B

Example 8

Introduction

The present invention is advantageous as it provides for novel phytases that have properties making them particularly useful and efficient as feed enzymes. In particular the invention relates to isolated and/or purified novel phytase polypeptides as described herein, or a functional fragment, or variants or modified forms thereof, or modified form thereof. The invention also provides the nucleic acid sequence encoding said phytase.

To be efficient as an enzyme additive to food or animal feed, the phytase has to combine a number of different properties. In order to be able to degrade phytic acid in the acidic environment of an animal's stomach it has to be active at low pH, preferably over a broad range of pH values. In addition, it has to have high specific activity and preferably high thermostability to enable the protein to withstand high temperatures commonly used in preparation of feedstuffs such as feed pellets.

It is also important that the enzyme has broad substrate specificity allowing it to hydrolyse not only phytate but also intermediate products of phytate degradation such as inositol pentaphosphates, tetraphosphates and triphosphates. Studies on phytate degradation in pigs show that these inositol oligophosphates otherwise remain largely insoluble in the small and large intestine and thus inaccessible to alkaline phosphatases produced by the animal and gut microflora. Variations in substrate specificity profiles of different enzymes have been identified. For example, inositol-triphosphates generated by the phytase from *B. subtilis* are essentially resistant to further hydrolysis by this enzyme.

Suitably these variants show improved characteristics with respect to any one of the following: temperature stability, pH range, pepsin stability, specific activity, substrate specificity, and broader substrate specificity. Suitable methods for determining these characteristics are disclosed herein.

In particular, the improvements in phytase characteristics are directed to the enzyme stability under food and feed processing conditions, to the enzyme stability during stomach transit, and to the enzyme activity and stability in human or animal stomach and/or intestinal tract making the improved variants particularly suitable for use as feed supplements. Thus, such improvements comprise among other parameters the increase in stability at elevated temperatures, preferably at temperatures above 65° C., the increase in stability against proteolytic digestion, preferably protease of the digestive tract such as pepsin, the increase in catalytic activity at low pH, preferably catalytic activity below pH 5.5, and the general efficiency of releasing phosphate groups from phytate, and preferably in addition inositol phosphates.

Improvements in phytase characteristics according to the present invention are directed to the use in food and feed processing as well as for the use as an additive to food and feed products. In particular, improvements are directed to the stability under food and feed processing conditions, to the stability during stomach transit, and to the activity and stability in human or animal stomach and/or intestinal tract. Such improvements comprise among other parameters the increase in stability at elevated temperatures, preferably at temperatures above 65° C., the increase in stability against proteolytic digestion, preferably protease of the digestive tract, the increase in catalytic activity at low pH, preferably catalytic activity below pH 5.5, and the general efficiency of releasing phosphate groups from phytate.

The increase in stability at elevated temperatures is quantified by the inactivation temperature of the enzyme. The inactivation temperature is defined as the temperature at which the residual activity of a phytase enzyme after incubation for a certain duration and subsequent cooling to room temperature is 50% of the residual activity of the same phytase enzyme incubated for the same duration under the same conditions at room temperature. Thermostability differences are the differences in ° C. between the inactivation temperatures of two enzymes.

Example 9

Pepsin Stability

Pepsin resistance at pH 2 of phytases from *Buttiauxella*, variants BP-17, BP-110, BP-111, and BP-112, compared to Phyzyme XP, Natuphos, and Ronozyme P
Materials and Methods
Buffers:
Pepsin incubation buffer: 0.1 M Glycine-HCl, pH 2.0, 3 mg/ml BSA, 2.9 mg Sodium chloride anhydrous/mL, 0.73 mg calcium chloride/mL. For solutions with pepsin, the incubation buffer is prepared to contain 500, 1000, 3000, 6000, or 10000 U/ml of pepsin (Sigma P-7000, 10000 U/mg corresponds to 27 mg/ml), respectively. One pepsin unit is defined as the amount of enzyme that will produce a $\Delta OD_{280}$ of 0.001 per min at pH 2.0 at 37° C., measured as TCA-soluble products using hemoglobin as substrate (Food Chemical Codex).
Phytase assay buffer: Acetate buffer 250 mM, pH 5.5

Phytase assay buffer with BSA: Acetate buffer 250 mM, pH 5.5, with 3 mg/ml BSA

Resistance Against Increasing Pepsin Concentration:

The set-ups for all enzymes were the same: Six samples with enzyme were prepared (in duplicate): Four samples with increasing amount of pepsin in buffer (pH 2), one sample without pepsin but in incubation buffer (pH 2), and one positive control sample with enzyme in assay buffer with BSA (pH 5.5).
For each sample, 900 µl incubation buffer without or with increasing amounts of pepsin or 900 µl assay buffer were mixed with 100 µl enzyme solution followed by incubation at 40° C. After 120 min incubation, 100 µl was withdrawn and mixed with 900 µl assay buffer. Samples were immediately analysed for phytase at pH 5.5 against phosphate standard curve as described by ISO draft international standard ISO/DIS 30024.

Results

Pepsin Resistence
The *Buttiauxella* variants all showed excellent stability towards pepsin at pH 2. In contrast, the activity of Natuphos was reduced dramatically already at a pepsin concentration of 500 U/ml, with further reduced activity finding a plateau of about 45% recovery at a pepsin concentration 3000 U/ml. The recovery of Ronozyme P was even worse with a reduction in recovery of less than 20% at a pepsin concentration of only 500 U/mg (FIG. 6A & Table 4).
FIG. 6 shows the resistance of the phytases originating from *Buttiauxella*, variants BP-17, BP-110, BP-111, and BP-112, and of Phyzyme XP, Natuphos, and Ronozyme P against increasing concentrations of pepsin. Data are relative to incubation at pH 2 without pepsin. A: all data points, B: same data but showing only more than 70% recovery.

TABLE 5

Same data as presented in FIG. 6

| Pepsin level | BP-17 | BP-17 v. 110 | BP-17 v. 111 | BP-17 v. 112 | Phyzyme XP | Natuphos | Ronozyme P, new |
|---|---|---|---|---|---|---|---|
| 0 | 100% | 100% | 100% | 100% | 100% | 100% | 100% |
| 500 | 87% | 96% | 98% | 85% |  | 61% | 19% |
| 1000 | 81% | 98% | 96% | 85% |  | 51% | 16% |
| 3000 | 82% | 96% | 94% | 84% | 93% | 44% | 17% |
| 6000 | 82% | 92% | 89% | 80% | 89% | 45% | 18% |
| 10000 | 86% | 95% | 94% | 79% | 98% | 46% | 21% |

Figure 6B:
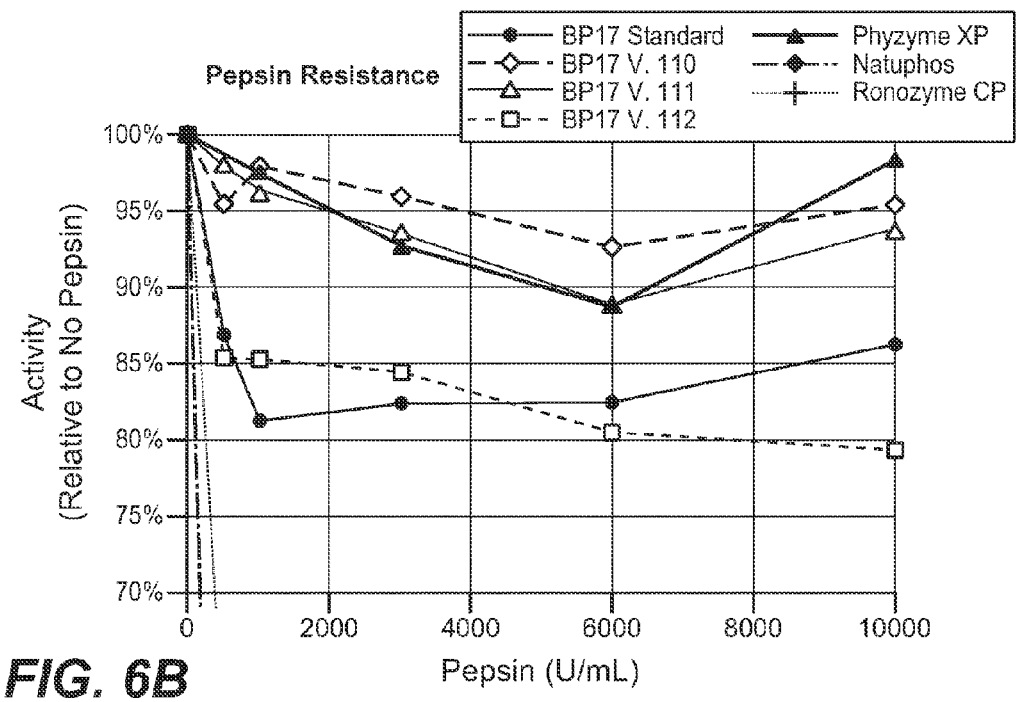

There are slight differences between the *Buttiauxella* variants, where variant BP-17 var.110 shows best stability having 95% activity left after two hours of incubation at the highest pepsin concentration, 10000 U/mL (FIG. 6B). In comparison, BP-17 showed a recovery of around 85% after two hours of incubation.
The *Buttiauxella* phytases also showed excellent acid stability. Comparing the activity measured at pH 5.5 after two hours of incubation at either pH 2 or pH 5.5 showed that all four *Buttiauxella* phytases did not lose activity during the 2 hours incubation at pH 2 whereas Phyzyme XP, Natuphos, and the new Ronozyme P showed slight to significant reduction in activity (Table 6).

TABLE 6

The activity measured at pH 5.5 after incubation in a buffer at pH 2 or pH 5.5 for two hours The numbers. are relative to the activity from the samples incubated at pH 5.5.

|  | BP-17 | BP-17 v. 110 | BP-17 v. 111 | BP-17 v. 112 | Phyzyme XP | Natuphos | Ronozyme P, new |
|---|---|---|---|---|---|---|---|
| Assay buffer | 100% | 100% | 100% | 100% | 100% | 100% | 100% |
| pH 2, no pepsin | 101% | 102% | 106% | 120% | 83% | 90% | 67% |

Data Summary

The *Buttiauxella* phytase variants according to the present invention show more than 75% recovery after 2 hours of incubation at pH 2, 37° C., 10000 U/ml of pepsin compared to activity of the sample incubated under the same condition but without pepsin present.

Example 10

Recovery of Enzyme Activity

Evaluation of Recovery of Enzyme Activity
Materials and Methods

Here, we evaluate the recovery of enzyme activity after pelleting of the wheat formulated enzyme. The enzyme is sprayed on granulated wheat and dried prior to mixing with feed followed by the pelleting process.

Figure 7:
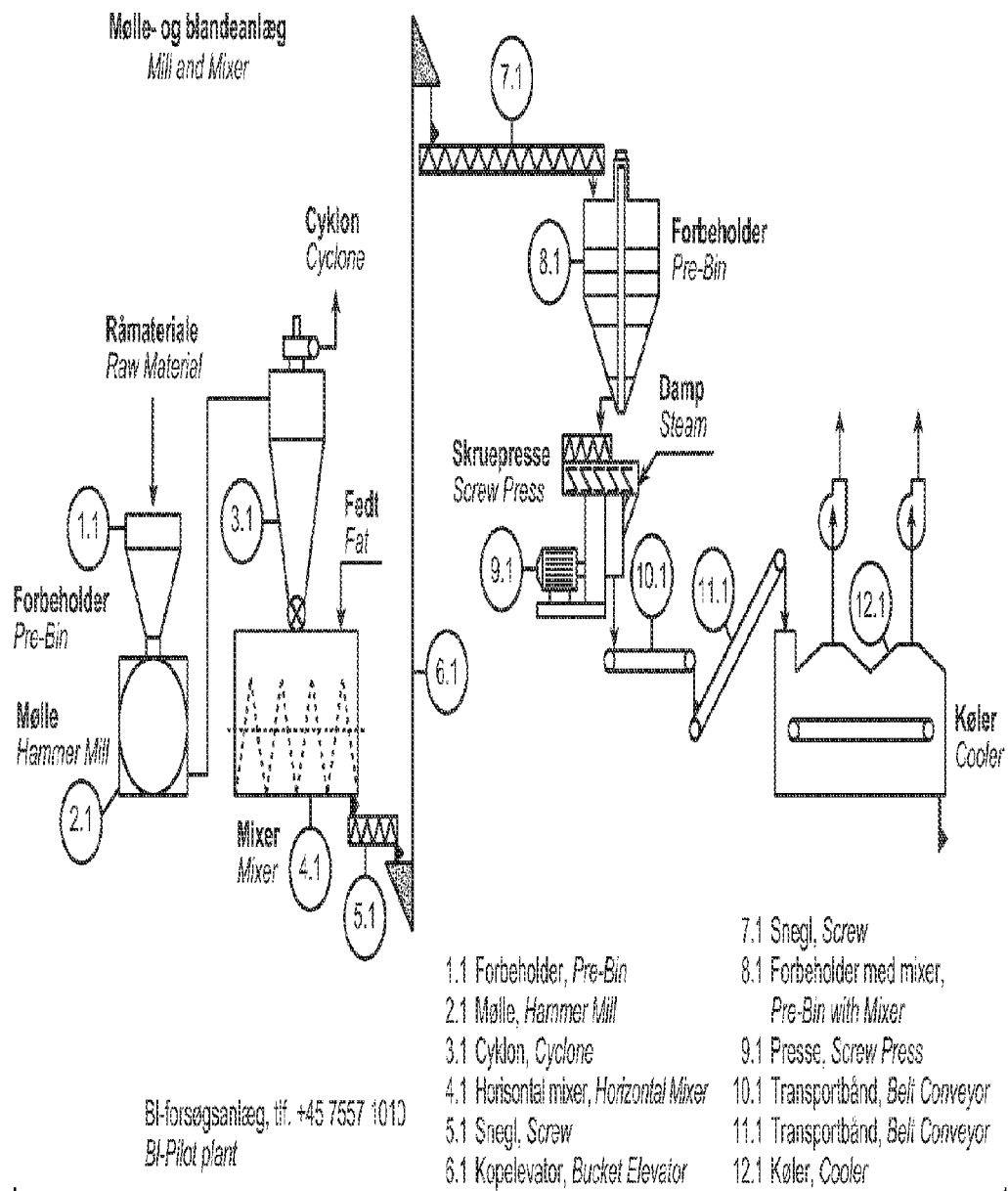
FIG. 7 shows a schematic diagram of the feed processing equipment (feed pelleting) used in Example 11.

Liquid enzymes where formulated on whole grounded wheat and dried to a dry matter content on approximately 90%. The inactivation of enzymes during thermal stress in the pelleting process was tested using a pelleting unit at the Technological Institute in Kolding (schematically presented in FIG. 7). Test sample is added to 10 kg premix and mixed for 10 min. Then 10 kg premix was added to 150 kg feed (large horizontal mixer) and mixed for 15 min. before conditioning/ steaming Feed is treated 30 sec. at 90° C./95° C. before pelleting. The temperature is measured in the outlet of the cascade mixer. Immediately after leaving the pelleting press the pellets are cooled to room temperature.

Phytase activity was measured according to the methodology recited in Example 10.

Phytase activity is 5 units per gm in the mash feed prior to pelletising.
Results The results are presented in FIGS. 8 to 10.

Figure 8:
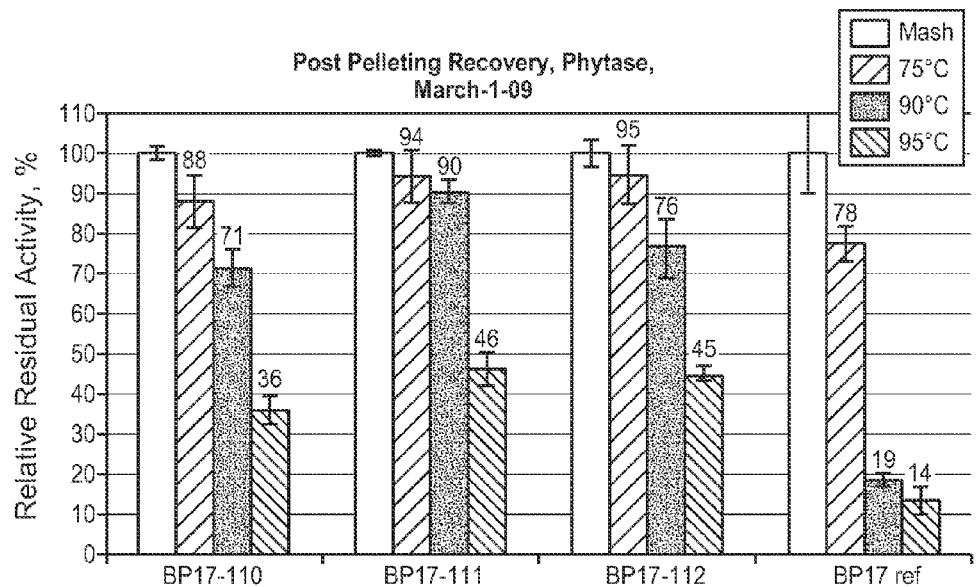
FIG. 8 shows data graphs.

In FIG. 8, the results from the pelleting trials of three Phytase B variants according to the present invention is disclosed. The enzymes were formulated on whole grounded wheat and dried to app 10% water content. Here, the recovery of phytase activity after pelleting for BP 17 var 111 is 90% at 90° C. compared to a recovery of 19% at 90° C. for the BP 17.

Figure 9:
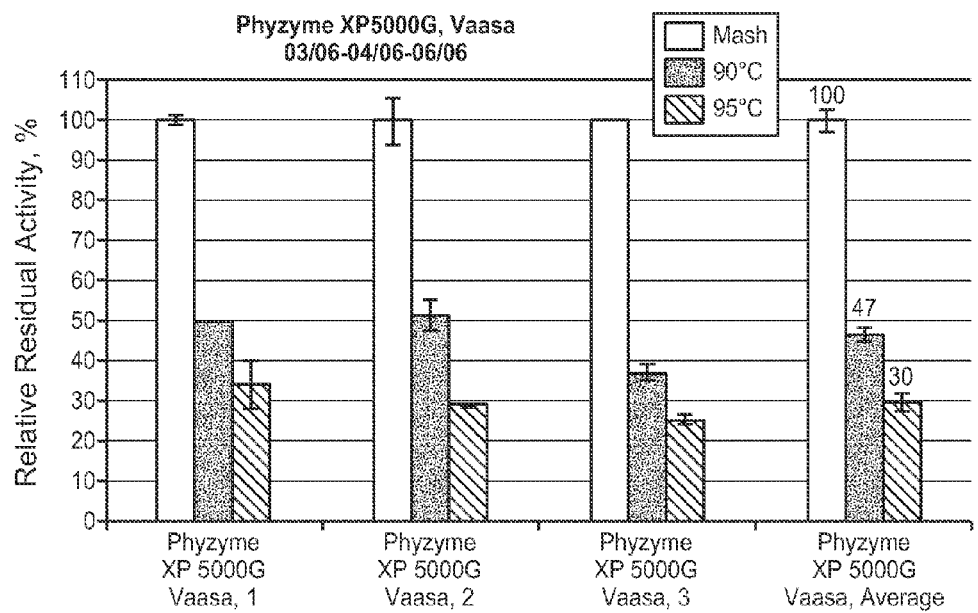
FIG. 9 shows data graphs.

As reference is the Phyzyme XP, an *E. coli* phytase was formulated on whole grounded wheat. The results are shown in FIG. 9. Here, the recovery of phytase activity after being pelletised at 90° C. from the three batches of Phyzyme XP formulated on whole grounded wheat is 47%.

Figure 10:
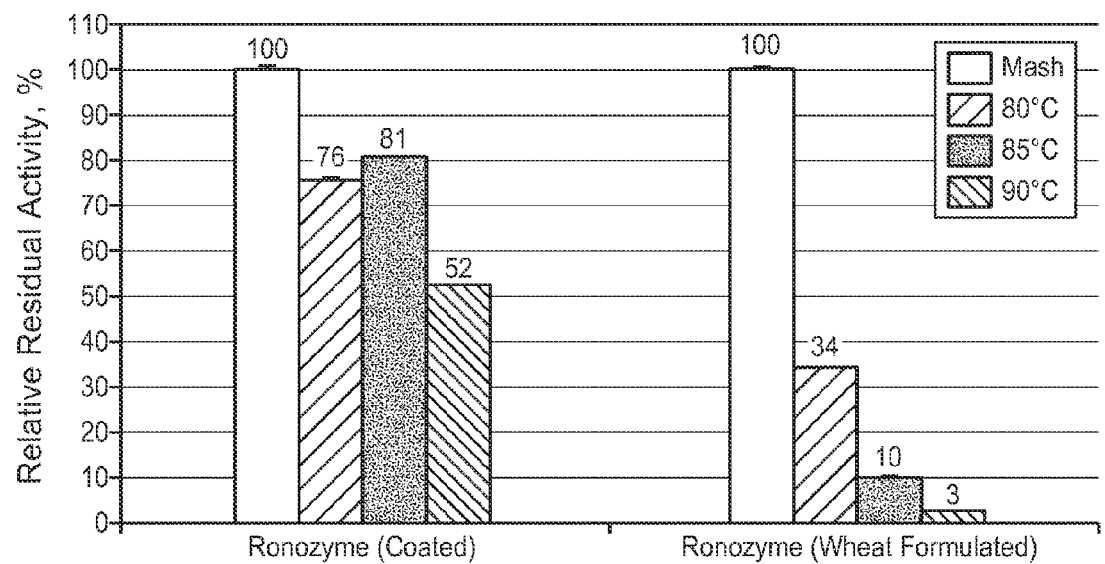
FIG. 10 shows data graphs.

Ronozyme was also tested. The product is sold in a coated version, to protect the enzyme from the heat in the pelleting process. In this trial the phytase was extracted from the coated product and formulated on whole grounded wheat to study the themostability of the phytase molecule without protection. The results are shown in FIG. 10.
Data Summary The *Buttiauxella* phytase variants of the present invention formulated on wheat show more than 70% recovery after being pelleted at 90° C.

Example 11

Phytic Acid Degradation

Results from a Study of Phytic Acid Degradation by Phytase Solutions

Three different buffers were used in the incubations. They were as follows:
  250 mM acetate pH 5.5;
  250 mM Acetate M pH 3.5; and
  250 mM HCl glycine pH 2.5.

All phytases used on the incubations were diluted in assay buffer to enzyme level at 1 U/ml.

The phytate substrate solution used in the incubation is a Phytate 1% (1 g/100 ml buffer).

The substrate is prepared in same buffer as used for the dilution of phytases to keep the pH level constant in the reaction.

The reaction is terminated by 1M HCl.
Incubation

The incubation volumes are: 1.5 or 3.0 ml Phytate+0.25 ml enzyme+3.25 or 1.75 ml buffer at 37° C., a total volume of 5.0 ml.

Sub-samples of 0.5 ml are taken at different time points (0, 30, 60 and 90 min).

Figure 11:
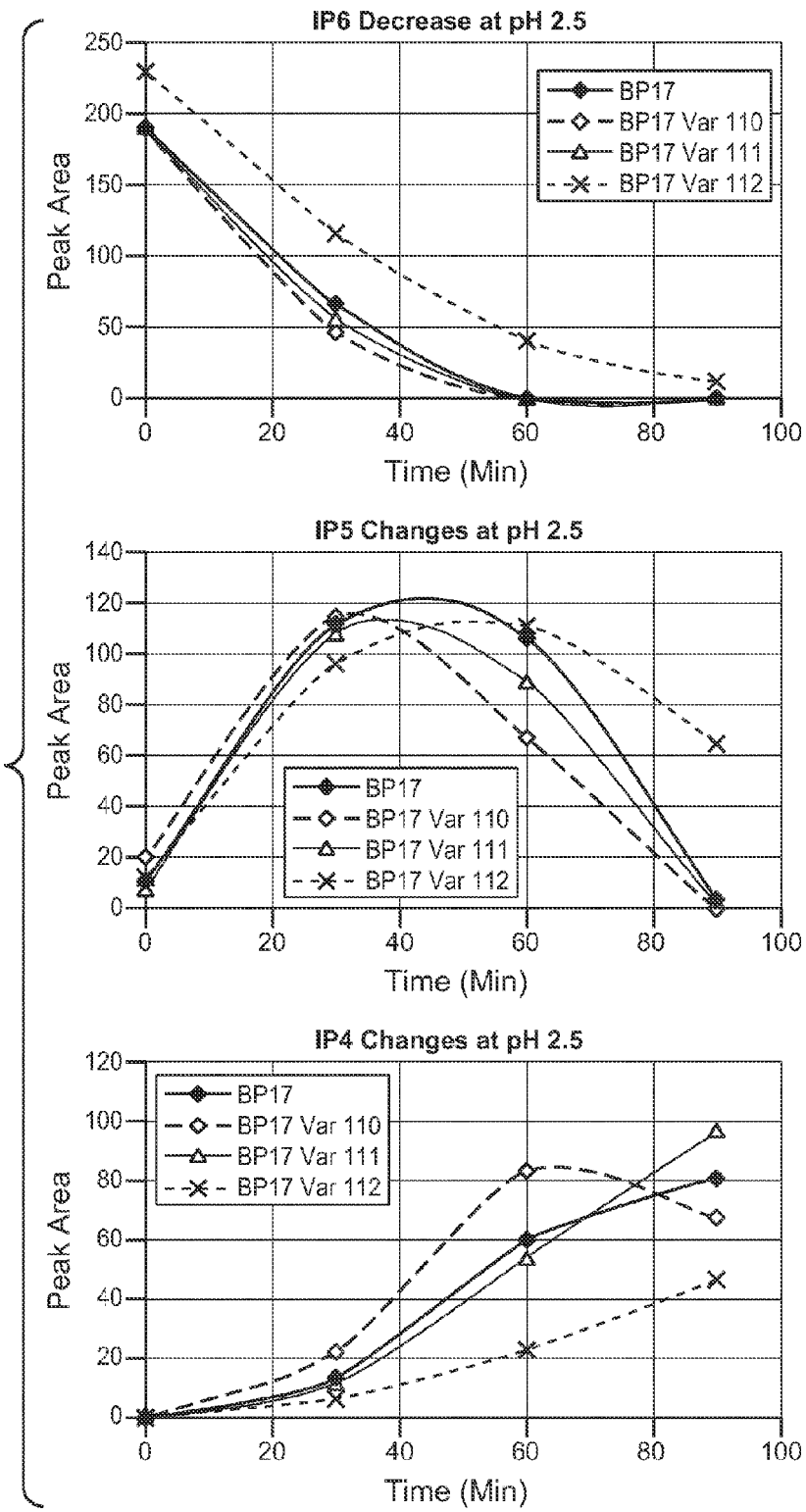
FIG. 11 shows data graphs.
Figure 12:
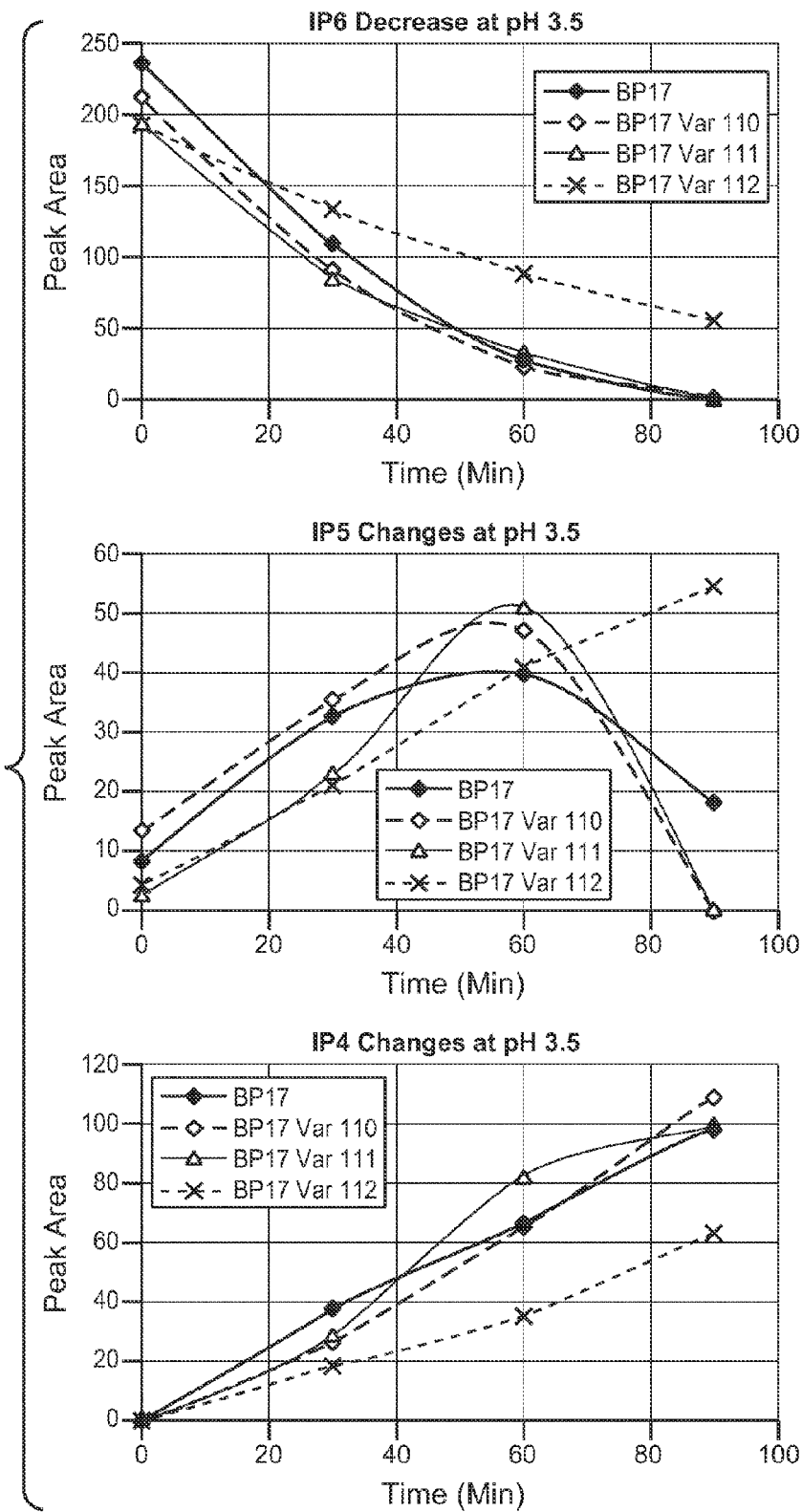
FIG. 12 shows data graphs.
Figure 13:
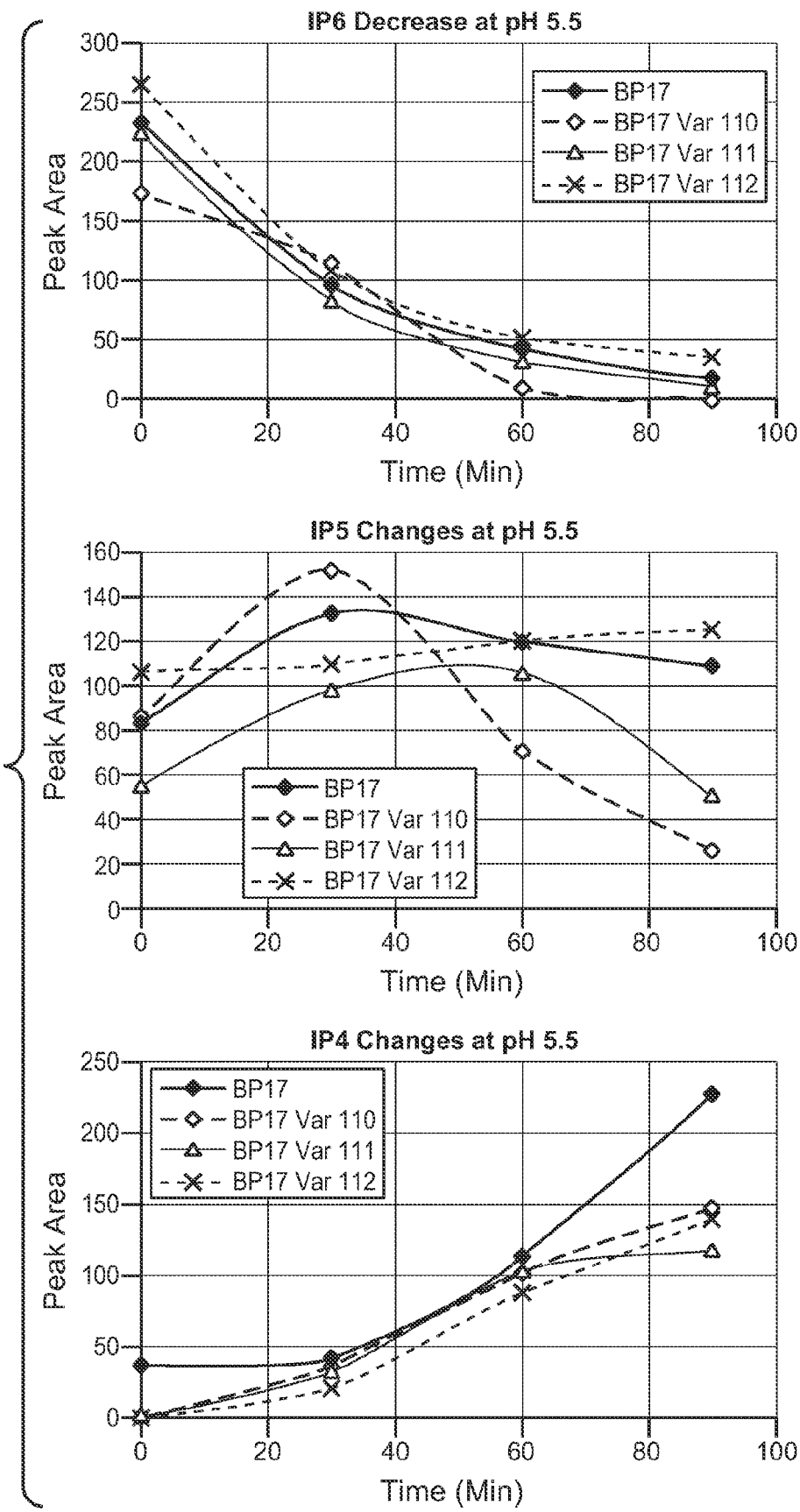
FIG. 13 shows data graphs.
Figure 14:
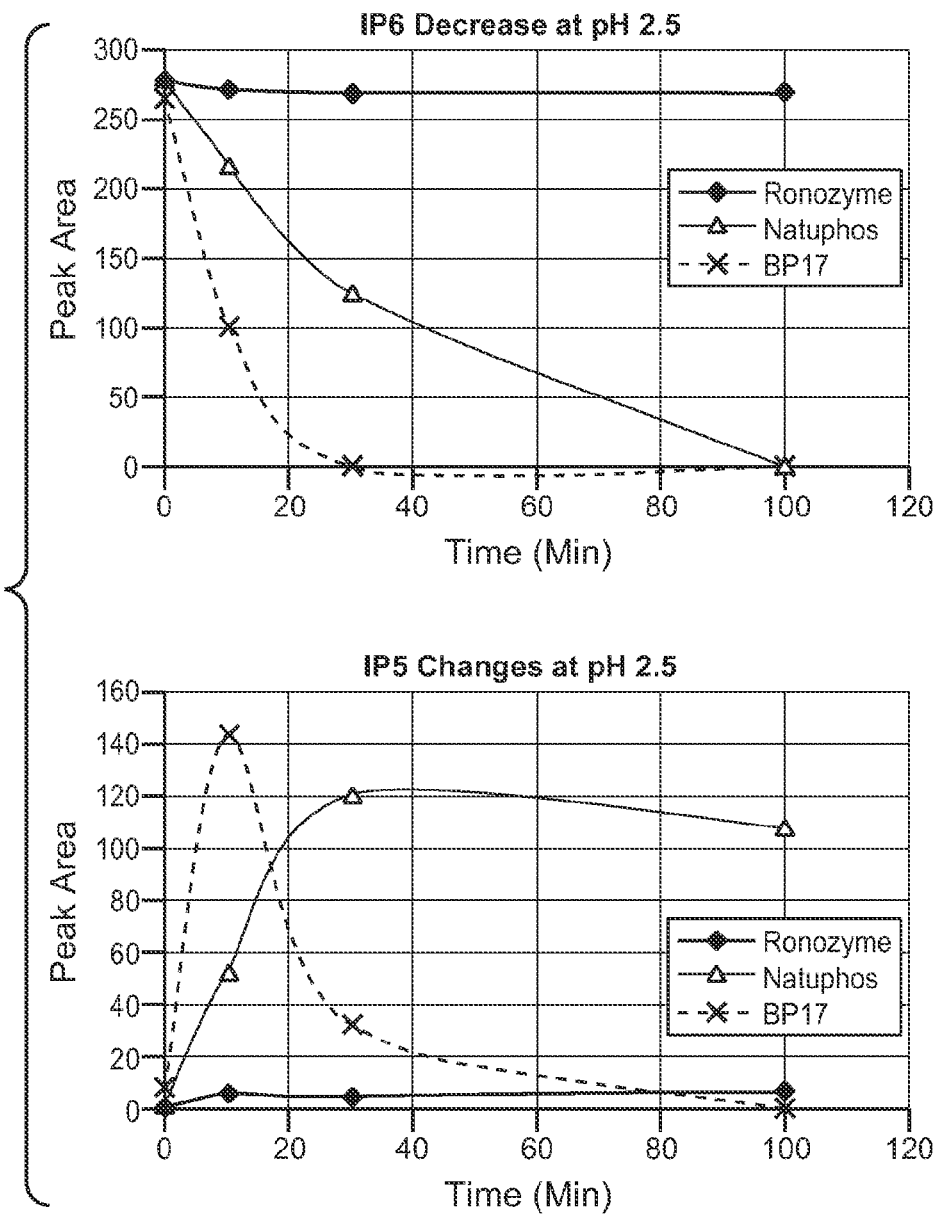
FIG. 14 shows data graphs.

An eppendorf tube is prepared with a 0.2 ml 1M HCl for each sub-sample prior to the sub-sampling. By blending the sub-sample from the incubation with HCl the enzyme reaction is terminated. Each sub-sample of 0.7 ml is stored at 4° C. until HPLC analysis.
HPLC Method Analysis of phytate and inositol isomers by high performance ion chromatography (HPIC). This method has been described by Skoglund and Carlsson et al. (*J. Agric. Food Chem.*, 45(1997), 451-4365. *J. Agric. Food Chem.*, 46 (1998), 1877-1882; and *J. Agric. Food Chem.*, 49(2001), 11695-1701. The column used was a strong anion exchanger (4×250 mm) from Dionex with a pre-column of 4×50 mm Solvent A, MilliQ water, Solvent B, 1N HCl prepared in water. The gradient is from 2.5% to 49% B in 30 min followed by 3 min of isocratic at 50% and 2 min isocratic at 2.5% at a flow of 0.8 ml/min Each run is 35 min. It is possible to reduce the run to totally 25 min as phytase does not produce so many theoretically possible IP isomers. The eluent was in-line derivatized with a water solution containing 0.1% $Fe(NO_3)_3.9HO_2$ and 2% perchloric acid ($HClO_4$) at a flow of 0.4 ml/min Phytate and IP isomers were detected at 290 nm as a positive peak. This is due to the formation of phytate-$Fe^{3+}$—$ClO_4^-$ complex. A perchloric acid solution of 60% was bought from Sigma.
Results The results are presented in FIGS. 11-14.
Data Summary All of the enzymes of the present invention display favourable characteristics. The phytases of the present invention break down phytate at all of the tested pH levels.
The enzymes of the present invention are very active at pH 5.5.
BP 110 and BP 111 display similar activity at pH 2.5 and 3.5.
BP 110 and BP 111 break down all the phytate added to the incubations after 90 min at both pH 2.5 and pH 3.5
BP112 breaks down 75% of the phytate added to the incubations after 90 min at both pH 2.5 and pH 3.5
The enzymes of the present invention display better characteristics than Ronozyme and Natuphos at pH 2.5 (see at least FIG. 14) (Enzyme concentration is higher than seen in FIGS. 11-13, so *Buttiauxella* BP17 is there as reference.)

Example 12

Phytic Acid Hydrolysis in a Liquefact

Phytic Acid Determination:
Phytic acid content: Phytic acid was extracted from a sample by adjusting the pH of the 5% slurry (if it is dry sample) to pH 10 and then determined by an HPLC method using an ion exchange column Phytic acid was eluted from the column using a NaOH gradient system. Phytic acid content in the liquid was then calculated by comparing to a phytic acid standard.

Results

Figure 15:
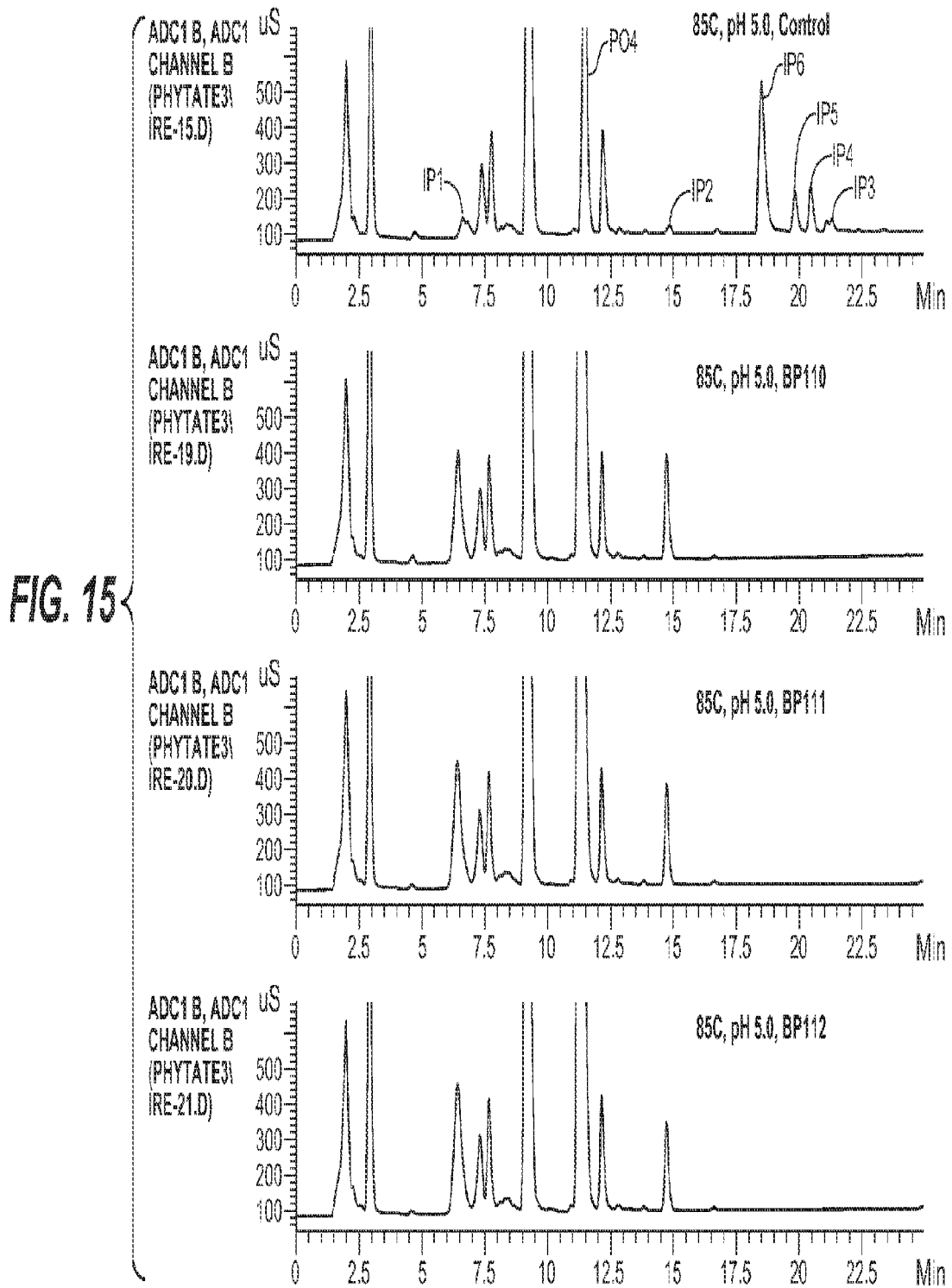
FIG. 15 shows HPLC data plots.
Figure 16:
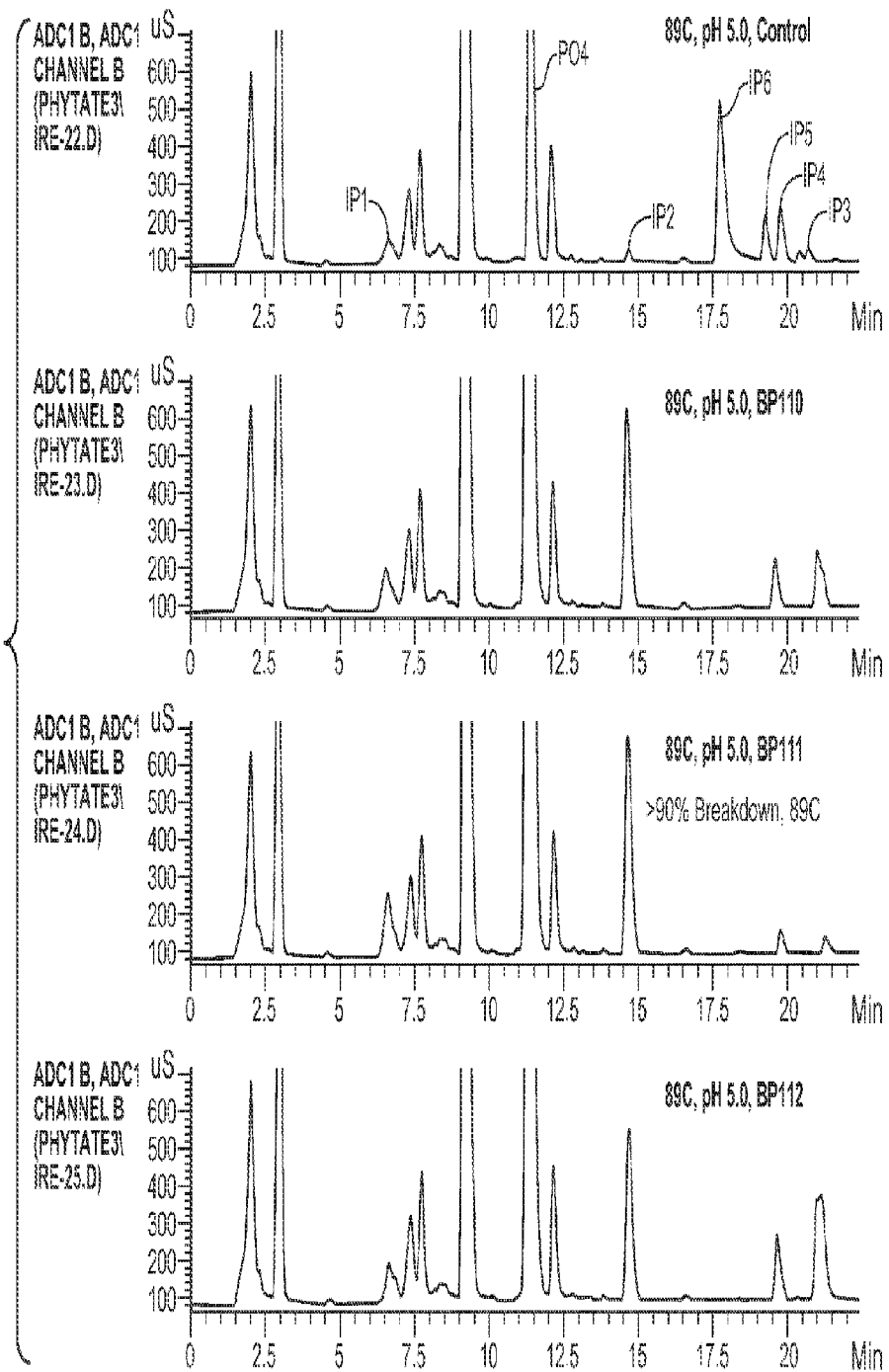
FIG. 16 shows HPLC data plots.

The effect of temperature on the hydrolysis of phytic acid of the whole ground corn liquefact from a conventional dry grind liquefaction process (source: Illinois River Energy, Monroe, Ill.) by different thermostable BP variant phytase, i.e., BP110, BP111 and BP112 was studied. The pH of a 32% ds ("dry solid") whole ground corn ds corn liquefact was adjusted to pH 5.0. and placed in a water bath maintained at 85° C. and 89° C. After temperature equilibration, BP-phytase was added at 4.0 FTU/gds. corn. Samples were then taken at 20 minutes and the enzyme reaction was terminated by the addition of 10 mM sodium hydroxide (diluted 1 to 10 fold). The diluted samples were then filtered and analyzed by HPLC for their phytate derivatives profile (IP1 to IP6). The HPLC chromatograms in FIGS. 15 and 16 clearly showed that phytase from all three variants catalyzed the hydrolysis of phytic acid at temperature greater than 85° C. The phytic acid content (phytic acid (IP6) and intermediates IP1 to IP5) in whole ground corn liquefact is around 1.7% ds.corn and data in FIG. 15 showed that more than 95% of the phytic acid was hydrolyzed by thermostable phytase under the current liquefaction conditions. Significantly, the HPLC profile from the samples incubated at 89° C. showed that the BP-111 phytase variant exhibited higher thermostability compared to phytase from two other variants (see FIG. 16; BP-110 and BP-112).

Summary Aspects

Summary aspects of the present invention will now described by way of numbered paragraphs.

1. A phytase variant having phytase activity and an amino acid sequence that varies from the amino acid sequence of the wild type *Buttiauxella* sp. phytase (SEQ ID NO: 1), wherein the amino acid sequence of the phytase variant comprises at least one variation as compared with SEQ ID NO: 1, and wherein the at least one variation occurs at a position selected from the group consisting of positions 75, 76 and 374 of SEQ ID NO: 1, and wherein each of said at least one variations can be the same or different and can comprise a substitution, deletion or insertion.
2. A phytase of paragraph 1, wherein the at least one variation comprises a variation of one, two or all three of the positions selected from the group consisting of: S75, Q76 and A374.
3. A phytase of paragraph 2, wherein the at least one variation comprises a variation selected from the group consisting of: S75P, Q76R and A374P.
4. A phytase of paragraphs 1 to 3, wherein the at least one variation also comprises a variation at one or more positions selected from the group consisting of: N37, G77, H160, F164, T171, S188, G192, K198, A235, Q256 and/or P367.
5. A phytase of paragraph 4, wherein the at least one variation comprises a variation selected from the group consisting of: N37Y, G77S, H160R, F164E, F164S, T171V, T171I, S188P, G192A, K198R, A235V, Q256P, Q256A, Q256E and/or P367L.
6. A phytase of paragraphs 1 to 5, wherein the at least one variation also comprises a variation at one or more positions selected from the group consisting of: A89, D92, T134, F164, T176, A178, K207, A209, S248, Q256, A261 and/or N270.
7. A phytase of paragraph 6, wherein the at least one variation comprises a variation at one or more positions selected from the group consisting of: A89T, D92A, T134I, F164S, T176K, A178P, K207E, A209S, S248L, Q256Y, A261E and/or N270K.
8. A phytase of paragraph 7, wherein said phytase comprises a sequence of SEQ ID NO: 2.
9. A phytase of any of paragraphs 1-8, wherein said phytase comprises a sequence comprising variations selected from the group consisting of:
a) N37Y, S75P, A89T, D92A, T134I, H160R, F164E, T171V, T176K, A178P, S188P, G192A, K198R, K207E, A209S, S248L, Q256Y, A261E, N270K, A374P
b) N37Y, G77S, A89T, D92A, T134I, H160R, F164E, T171V, T176K, A178P, S188P, G192A, K198R, K207E, A209S, S248L, Q256Y, A261E, N270K, A374P c) N37Y, S75P, Q76R, A89T, D92A, T134I, H160R, F164E, T171I, T176K, A178P, S188P, G192A, K207E, A209S, A235V, S248L, Q256Y, A261E, N270K, A374P
d) N37Y, A89T, D92A, T134I, F164E, T171V, T176K, A178P, G192A, K207E, A209S, A235V, S248L, Q256P, A261E, N270K, A374P
e) S75P, Q76R, A89T, D92A, T134I, H160R, F164E, T171I, T176K, A178P, S188P, G192A, K207E, A209S, S248L, Q256Y, A261E, N270K, A374P
f) N37Y, Q76R, A89T, D92A, T134I, H160R, F164E, T171I, T176K, A178P, S188P, G192A, K207E, A209S, S248L, Q256Y, A261E, N270K, A374P
g) N37Y, Q76R, A89T, D92A, T134I, F164S, T171V, T176K, A178P, S188P, G192A, K207E, A209S, A235V, S248L, Q256A, A261E, N270K, A374P
h) S75P, A89T, D92A, T134I, F164E, T171V, T176K, A178P, S188P, G192A, K207E, A209S, A235V, S248L, Q256Y, A261E, N270K, A374P
i) S75P, Q76R, A89T, D92A, T134I, H160R, F164E, T171V, T176K, A178P, S188P, G192A, K207E, A209S, A235V, S248L, Q256Y, A261E, N270K, P367L, A374P
j) N37Y, A89T, D92A, T134I, F164E, T171I, T176K, A178P, G192A, K207E, A209S, A235V, S248L, Q256Y, A261E, N270K, A374P
k) N37Y, Q76R, A89T, D92A, T134I, F164E, T171V, T176K, A178P, G192A, K207E, A209S, S248L, Q256Y, A261E, N270K, A374P
l) N37Y, Q76R, A89T, D92A, T134I, F164E, T171V, T176K, A178P, G192A, K207E, A209S, S248L, Q256A, A261E, N270K, A374P
m) N37Y, S75P, Q76R, A89T, D92A, T134I, F164E, T171V, T176K, A178P, K207E, A209S, A235V, S248L, Q256A, A261E, N270K, A374P
n) N37Y, S75P, A89T, D92A, T134I, H160R, F164E, T171V, T176K, A178P, K207E, A209S, A235V, S248L, Q256Y, A261E, N270K, A374P
o) N37Y, A89T, D92A, T134I, H160R, F164S, T171I, T176K, A178P, S188P, G192A, K207E, A209S, A235V, S248L, Q256E, A261E, N270K, A374P
p) A89T, D92A, T134I, H160R, F164E, T171V, T176K, A178P, G192A, K207E, A209S, A235V, S248L, Q256Y, A261E, N270K, A374P
q) N37Y, S75P, A89T, D92A, T134I, H160R, F164S, T171V, T176K, A178P, S188P, K207E, A209S, S248L, Q256H, A261E, N270K, A374P
r) N37Y, S75P, A89T, D92A, T134I, F164S, T171V, T176K, A178P, S188P, G192A, K207E, A209S, S248L, Q256A, A261E, N270K, A374P
s) S75P, Q76R, A89T, D92A, T134I, H160R, F164E, T171V, T176K, A178P, G192A, K207E, A209S, S248L, Q256A, A261E, N270K, A374P; and t) N37Y, Q76R, A89T, D92A, T134I, H160R, F164S, T171V, T176K, A178P, G192A, K207E, A209S, A235V, S248L, Q256Y, A261E, N270K, A374P.

10. A phytase which has at least a minimum percent sequence identity and/or percent homology to the phytase of any of paragraphs 1-9, wherein the minimum percent identity and/or homology is selected from the group consisting of at least 50%, at least 60%, at least 75%, at least 80%, at least 85%, at least 90%, at least 93%, at least 95%, at least 96%, at least 97%, at least 98%, and at least 99%.

11. A phytase of any of paragraphs 1 to 10 having at least one improved property as compared to the phytase of SEQ ID NO: 1, wherein the improved property is selected from the group consisting of increased specific activity; decreased sensitivity to one or more proteases; increased thermal activity; increased thermal stability, increased stability in an acidic pH, enhanced stability in a basic pH, increased feed processing stability.

12. A phytase of paragraphs 10, wherein the at least one improved property is a decreased sensitivity to one or more proteases found in an animal selected from the group consisting of humans, alpaca, bison, camel, cattle, chicken, poultry, chinchilla, deer, donkey, duck, fish, frog, goat, goose, fowl, horse, llama, mink, mule, ostrich, pigeon, reindeer, sheep, shellfish, swine, turkey, yak, water buffalo cat, chimpanzee, dog, ferret, gerbil, goldfish, guinea pig, hamster, monkey, parakeet, reptiles and rodents.

13. A phytase of any of paragraphs 1-11, which has prolonged activity, as compared to the phytase of SEQ. ID NO: 1, in the digestive tract of an animal selected from the group consisting of humans, alpaca, bison, camel, cattle, chicken, poultry, chinchilla, deer, donkey, duck, fish, frog, goat, goose, fowl, horse, llama, mink, mule, ostrich, pigeon, reindeer, sheep, shellfish, swine, turkey, yak, water buffalo cat, chimpanzee, dog, ferret, gerbil, goldfish, guinea pig, hamster, monkey, parakeet, reptiles and rodents.

14. A nucleic acid encoding a phytase of any of paragraphs 1 to 13.

15. A vector comprising the nucleic acid of paragraph 14.

16. A host cell comprising the nucleic acid of paragraph 14.

17. An enzyme composition comprising at least one phytase of any of paragraphs 1 to 13.

18. An enzyme composition comprising at least one phytase of any of paragraphs 1 to 13, wherein said composition is useful in starch liquefection.

19. A method for producing a phytase variant of any of paragraphs 1 to 13 in a host cell, comprising
   a) transforming a host cell with a DNA construct comprising the nucleic acid encoding the phytase of any of paragraphs 1 to 13, and
   b) cultivating the transformed host cell in a suitable culture medium.

20. The method according to paragraph 19, wherein the host cell is selected from the group consisting of a fungal cell, a bacterial cell or a plant cell.

21. A phytase variant having phytase activity and an amino acid sequence that varies from the amino acid sequence of the wild type *Buttiauxella* sp. phytase (SEQ ID NO: 1), wherein the amino acid sequence of the phytase variant comprises at least one variation as compared with SEQ ID NO: 1, and wherein the variant has a variation at at least one or more of the following positions: 70, 193, 197, 221 and 407. Preferably, the variant has a variation at at least two or more of the following positions: 70, 193, 197, 221 and 407. Preferably, the variant has a variation at at least three or more of the following positions: 70, 193, 197, 221 and 407. Preferably, the variant has a variation at at least four or more of the following positions: 70, 193, 197, 221 and 407. Preferably, the variant has a variation at at least the following positions: 70, 193, 197, 221 and 407.

22. A phytase of paragraph 21, wherein the variant has at least the following variations: N70Y, H193R, F197E, S221P and A407P.

23. A method for production of food or animal feed comprising a step of admixing a polypeptide as paragraphed in any of paragraphs 1 to 13 or 21 to 22 or an enzyme composition according to paragraph 17 or paragraph 18 or prepared by the method of paragraph 19 or 20 with another food or feed ingredient to form said food or animal feed.

24. A method for production of food or animal feed comprising a step of spraying a polypeptide as paragraphed in any of paragraphs 1 to 13 or 21 to 22 or an enzyme composition according to paragraph 17 or paragraph 18 or prepared by the method of paragraph 19 or 20 in liquid form onto said food or animal feed.

25. A method for production of food or animal feed comprising a step of mixing a polypeptide as paragraphed in any of paragraphs 1 to 13 or 21 to 22 or an enzyme composition according to paragraph 17 or paragraph 18 or prepared by the method of paragraph 19 or 20 as a dry product with said food or animal feed.

26. A method for production of animal feed comprising a step of admixing a polypeptide as paragraphed in any of paragraphs 1 to 13 or 21 to 22 or an enzyme composition according to paragraph 17 or paragraph 18 or prepared by the method of paragraph 19 or 20 with another food or feed ingredient to form said animal feed.

27. A method for production of animal feed comprising a step of spraying a polypeptide as paragraphed in any of paragraphs 1 to 13 or 21 to 22 or an enzyme composition according to paragraph 17 or paragraph 18 or prepared by the method of paragraph 19 or 20 in liquid form onto said animal feed.

28. A method for production of animal feed comprising a step of mixing a polypeptide as paragraphed in any of paragraphs 1 to 13 or 21 to 22 or an enzyme composition according to paragraph 17 or paragraph 18 or prepared by the method of paragraph 19 or 20 as a dry product with said animal feed.

29. A food or animal feed composition comprising either i) a phytase as paragraphed in any of paragraphs 1 to 13 or 21 to 22 or an enzyme composition according to paragraph 17 or paragraph 18 or prepared by the method of paragraph 19 or 20 and/or ii) a food or animal feed produced by the method according to any one of paragraphs 23 to 28.

30. An animal feed composition comprising either i) a phytase as paragraphed in any of paragraphs 1 to 13 or 21 to 22 or an enzyme composition according to paragraph 17 or paragraph 18 or prepared by the method of paragraph 19 or 20 and/or ii) an animal feed produced by the method according to any one of paragraphs 23 to 28.

31. Use of a phytase polypeptide as paragraphed in any of paragraphs 1 to 13 or 21 to 22 or an enzyme composition according to paragraph 17 or paragraph 18 or prepared by the method of paragraph 19 or 20 in food or animal feed.

32. Use of a phytase polypeptide as paragraphed in any of paragraphs 1 to 13 or 21 to 22 or an enzyme composition according to paragraph 17 or paragraph 18 or prepared by the method of paragraph 19 or 20 in an animal feed.

33. A method of reducing the levels of phosphorus in animal manure, characterized in that an animal is fed with a phytase polypeptide as paragraphed in any of paragraphs 1 to 13 or 21 to 22 or an enzyme composition according to paragraph 17 or paragraph 18 or prepared by the method of paragraph 19 or 20 or a feed according to paragraph 29 or 30, and wherein said phytase is in an amount effective in converting phytate contained in said animal feed.

34. Use of a phytase polypeptide as paragraphed in any of paragraphs 1 to 13 or 21 to 22 or an enzyme composition according to paragraph 17 or paragraph 18 or prepared by the method of paragraph 19 or 20 or a feed according to paragraph 29 or 30, in the manufacture of an animal feed to reduce the levels of phosphorus in manure from the animal fed with said phytase polypeptide.

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An isolated phytase variant having phytase activity and an amino acid sequence that varies from the amino acid sequence of the wild type *Buttiauxella* sp. phytase of SEQ ID NO: 1, wherein the amino acid sequence of the phytase variant comprises a variation at one or more positions corresponding to positions 75, 76, 77, 198, 367 or 374 of SEQ ID NO: 1, and wherein the amino acid sequence of the phytase variant is 90% identical to SEQ ID NO: 1.

2. The phytase variant of claim 1, wherein the phytase variant further comprises one or more additional variations, wherein the additional variations are substitutions corresponding to substitutions in SEQ ID NO: 1 selected from the group consisting of D92A, F164E, F164S, T171V, T171I, G192A, Q256A, Q256E, and Q256P.

3. The phytase variant of claim 2, wherein the phytase variant comprises one or more substitutions corresponding to substitutions in SEQ ID NO: 1 selected from the group consisting of S75P, Q76R, G77S, K198R, P367L, and A374P.

4. The phytase variant of claim 3, wherein the phytase variant further comprises one or more additional variations at positions corresponding to positions of SEQ ID NO: 1 selected from the group consisting of positions 26, 37, 89, 134, 160, 176, 178, 188, 190, 207, 209, 211, 235, 261, 270, 303 and 318.

5. The phytase variant of claim 4, wherein the one or more additional variations are substitutions corresponding to substitutions in SEQ ID NO: 1 selected from the group consisting of K26E, N37Y, A89T, T134I, T134V, H160R, T176K, A178P, S188N, D190E, K207E, K207T, A209S, D211C, A235V, A261E, N270K, I303F and N318D.

6. The phytase variant of claim 5, wherein the phytase variant further comprises one or more additional variations at positions corresponding to positions of SEQ ID NO: 1 selected from the group consisting of positions 1, 10, 11, 38, 66, 71, 81, 92, 109, 111, 119, 120, 121, 141, 142, 152, 155, 193, 214, 239, 245, 248, 255, 268, 277, 283, 285, 287, 288, 293, 296, 314, 337, 345, 350, 364, 371, 372, 396, 399, 406 and 413.

7. The phytase variant of claim 6, wherein the one or more additional variations are substitutions corresponding to substitutions in SEQ ID NO: 1 selected from the group consisting of N1S, V10I, E11I, T38S, Q66E, Q71K, T81A, D92E, Q141R, V142L, T152M, D155E, L193Q, D211C, I214V, A235V, N239K, E245D, S248L, V255A, A261E, R268A, R268T, N270K, A277T, N283D, N285K, T287D, E288A, D293G and P296S.

8. An enzyme composition comprising the phytase variant according to claim 1, further comprising one or more of a glucoamylase, an alpha-amylase, a protease, a pullulanase, an isoamylase, a cellulase, a hemicellulase, a xylanase, a cyclodextrin glycotransferase, a lipase, a laccase, an oxidase, an esterase, a cutinase, another phytase or any combinations thereof.

9. The enzyme composition of claim 8, wherein an alpha-amylase is included.

* * * * *

SEQUENCE LISTING

```
<160> NUMBER OF SEQ ID NOS: 7

<210> SEQ ID NO 1
<211> LENGTH: 413
<212> TYPE: PRT
<213> ORGANISM: Buttiauxella sp.
<220> FEATURE:
<221> NAME/KEY: misc_feature
<223> OTHER INFORMATION: Fig. 1 - Amino acid sequence of wild-type
      Buttiauxella sp. P1-29 phytase

<400> SEQUENCE: 1

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255
```

```
Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
                275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
                355                 360                 365

Ser Leu Asn Gln Pro Ala Gly Ser Val Gln Leu Lys Ile Pro Gly Cys
        370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 2
<211> LENGTH: 413
<212> TYPE: PRT
<213> ORGANISM: Buttiauxella sp.
<220> FEATURE:
<221> NAME/KEY: misc_feature
<223> OTHER INFORMATION: Fig. 2 - Amino acid sequence of a variant of
      Buttiauxella sp. P1-29 phytase

<400> SEQUENCE: 2

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Tyr Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Pro Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln Arg
145                 150                 155                 160

Tyr Ile Pro Glu Leu Ala Leu Met Asn Thr Val Leu Asn Phe Ser Lys
                165                 170                 175

Ser Pro Trp Cys Gln Lys His Ser Ala Asp Lys Pro Cys Asp Leu Ala
            180                 185                 190

Leu Ser Met Pro Ser Arg Leu Ser Ile Lys Asp Asn Gly Asn Glu Val
        195                 200                 205
```

```
Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Pro Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 3
<211> LENGTH: 1242
<212> TYPE: DNA
<213> ORGANISM: Buttiauxella sp.
<220> FEATURE:
<221> NAME/KEY: misc_feature
<223> OTHER INFORMATION: Fig. 3 - A nucleic acid sequence encoding the
      sequence of a wild-type Buttiauxella sp. P1-29
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1202)..(1202)
<223> OTHER INFORMATION: n is a, c, g, or t

<400> SEQUENCE: 3
aacgacactc ccgcttcagg ctaccaggtt gagaaagtgg taatactcag ccgccacggg      60
gtgcgagcac caaccaaaat gacacagacc atgcgcgacg taacacctaa tacctggccc    120
gaatggccag taaaattggg ttatatcacg ccacgcggtg agcatctgat tagcctgatg    180
ggcgggtttt atcgccagaa gtttcaacaa cagggcattt tatcgcaggg cagttgcccc    240
acaccaaact caattatgt ctgggcagac gttgatcagc gcacgcttaa aactggcgaa    300
gctttcctgg cagggcttgc tccggaatgt catttaacta ttcaccacca gcaggacatc    360
aaaaaagccg atccgctgtt ccatccggtg aaagcgggca cctgttcaat ggataaaact    420
caggtccaac aggccgttga aaagaagct caaacccca ttgataatct gaatcagcac    480
tatattccct ttctggcctt gatgaatacg accctcaact tttcgacgtc ggcctggtgt    540
cagaaacaca gcgcgataa aagctgtgat ttagggctat ccatgccgag caagctgtcg    600
```

```
ataaaagata atgg caacaa agtcgctctc gacggggcca ttggccttc gtctacgctt      660
gctgaaattt tcctgctgga atatgcgcaa gggatgccgc aagcggcgtg ggggaatatt      720
cattcagagc aagagtgggc gtcgctactg aaactgcata cgtccagtt tgatttgatg       780
gcacgcacgc cttatatcgc cagacataac ggcacgcctt tattgcaggc catcagcaac      840
gcgctgaacc cgaatgccac cgaaagcaaa ctgcctgata tctcacctga caataagatc      900
ctgtttattg ccggacacga taccaatatt gccaatatcg caggcatgct caacatgcgc      960
tggacgctac ctgggcaacc cgataacacc cctccgggcg gcgctttagt ctttgagcgt     1020
ttggccgata agtcagggaa acaatatgtt agcgtgagca tggtgtatca gactctcgag     1080
cagttgcgct cccaaacacc acttagcctt aatcaacctg cgggaagcgt acagctaaaa     1140
attcctggct gtaacgatca gacggctgaa ggatantgcc cgctgtcgac gttcactcgc     1200
gnggttagcc aaagcgtgga accaggctgc cagctacagt aa                        1242
```

```
<210> SEQ ID NO 4
<211> LENGTH: 1242
<212> TYPE: DNA
<213> ORGANISM: Buttiauxella sp.
<220> FEATURE:
<221> NAME/KEY: misc_feature
<223> OTHER INFORMATION: Fig. 4 - Nucleic acid sequence of an
      advantageous variant

<400> SEQUENCE: 4
aacgacactc ccgcttcagg ctaccaggtt gagaaagtgg taatactcag ccgccacggg       60
gtgcgagcac caaccaaaat gacacagacc atgcgcgacg taacaccta tacctggccc      120
gaatggccag taaaattggg ttatatcacg ccacgcggtg agcatctgat tagcctgatg      180
ggcgggtttt atcgccagaa gtttcaacaa caagggcatt taccgcaggg cagttgcccc     240
acaccaaact caattatgt ctggacagac gttgcgcagc gcacgcttaa aactggcgaa      300
gctttcctgg cagggcttgc tccgcaatgt ggtttaacta ttcaccacca gcagaatctt     360
gaaaaagccg atccgctgtt ccatccggtg aaagcgggca tctgttcaat ggataaaact     420
caggtccaac aggccgttga aaagaagct caaaccccca ttgataatct gaatcagcgc      480
tatattcccg agctggcctt gatgaatacg gttctcaact tttcgaaatc gccctggtgt     540
cagaaacaca gcgcggataa accctgtgat ttagccctat ccatgccgag caggctgtcg    600
ataaaagata atggcaacga agtctctctc gacggggcca ttggccttc gtctacgctt     660
gctgaaattt tcctgctgga atatgcgcaa gggatgccgc aagcggcgtg ggggaatatt     720
cattcagagc aagagtgggc gttgctactg aaactgcata cgtctatttt tgatttgatg    780
gaacgcacgc cttatatcgc cagacataaa ggcacgcctt tattgcaggc catcagcaac    840
gcgctgaacc cgaatgccac cgaaagcaaa ctgcctgata tctcacctga caataagatc    900
ctgtttattg ccggacacga taccaatatt gccaatatcg caggcatgct caacatgcgc    960
tggacgctac ctgggcaacc cgataacacc cctccgggcg gcgctttagt ctttgagcgt   1020
ttggccgata agtcagggaa acaatatgtt agcgtgagca tggtgtatca gactctcgag   1080
cagttgcgct cccaaacacc acttagcctt aatcaacctc ccggaagcgt acagctaaaa   1140
attcctggct gtaacgatca gacggctgaa ggatactgcc cgctgtcgac gttcactcgc   1200
gtggttagcc aaagcgtgga accaggctgc cagctacagt aa                      1242
```

```
<210> SEQ ID NO 5
<211> LENGTH: 413
<212> TYPE: PRT
```

<213> ORGANISM: Buttiauxella sp.
<220> FEATURE:
<221> NAME/KEY: misc_feature
<223> OTHER INFORMATION: BP-17 variant of Buttiauxella sp. Phytase

<400> SEQUENCE: 5

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
```

```
                385                 390                 395                 400
Val Val Ser Gln Ser Val Glu Pro Gly Cys Gln Leu Gln
                    405                 410

<210> SEQ ID NO 6
<211> LENGTH: 413
<212> TYPE: PRT
<213> ORGANISM: Buttiauxella sp.
<220> FEATURE:
<221> NAME/KEY: misc_feature
<223> OTHER INFORMATION: BP-110 variant of Buttiauxella sp. Phytase

<400> SEQUENCE: 6

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Tyr Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Ser Gln Ser Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln Arg
145                 150                 155                 160

Tyr Ile Pro Glu Leu Ala Leu Met Asn Thr Val Leu Asn Phe Ser Lys
                165                 170                 175

Ser Pro Trp Cys Gln Lys His Ser Ala Asp Lys Pro Cys Asp Leu Ala
            180                 185                 190

Leu Ser Met Pro Ser Arg Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
```

```
            340                 345                 350
Ser Met Val Tyr Gln Thr Leu Glu Gln Leu Arg Ser Gln Thr Pro Leu
        355                 360                 365

Ser Leu Asn Gln Pro Pro Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 7
<211> LENGTH: 413
<212> TYPE: PRT
<213> ORGANISM: Buttiauxella sp.
<220> FEATURE:
<221> NAME/KEY: misc_feature
<223> OTHER INFORMATION: BP-111 variant of Buttiauxella sp. Phytase

<400> SEQUENCE: 7

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Tyr Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Pro Arg Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln Arg
145                 150                 155                 160

Tyr Ile Pro Glu Leu Ala Leu Met Asn Thr Ile Leu Asn Phe Ser Lys
                165                 170                 175

Ser Pro Trp Cys Gln Lys His Ser Ala Asp Lys Pro Cys Asp Leu Ala
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Val Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
```

```
                    290             295             300
Gly His Asp Thr Asn Ile Ala Asn Ile Ala Gly Met Leu Asn Met Arg
305                 310             315                 320

Trp Thr Leu Pro Gly Gln Pro Asp Asn Thr Pro Pro Gly Gly Ala Leu
                325             330                 335

Val Phe Glu Arg Leu Ala Asp Lys Ser Gly Lys Gln Tyr Val Ser Val
                340             345             350

Ser Met Val Tyr Gln Thr Leu Glu Gln Leu Arg Ser Gln Thr Pro Leu
            355             360             365

Ser Leu Asn Gln Pro Pro Gly Ser Val Gln Leu Lys Ile Pro Gly Cys
        370             375             380

Asn Asp Gln Thr Ala Glu Gly Tyr Cys Pro Leu Ser Thr Phe Thr Arg
385             390             395                 400

Val Val Ser Gln Ser Val Glu Pro Gly Cys Gln Leu Gln
                405             410
```